United States Patent
Westbrook et al.

(10) Patent No.: US 6,811,538 B2
(45) Date of Patent: Nov. 2, 2004

(54) SLEEP APNEA RISK EVALUATION

(75) Inventors: Philip R. Westbrook, Newport Beach, CA (US); Daniel J. Levendowski, Carlsbad, CA (US); Milenko Cvetinovic, Vista, CA (US); Chris Berka, Carlsbad, CA (US); Yury Furman, Los Angeles, CA (US)

(73) Assignee: Ares Medical, Inc., Carlsbad, CA (US)

( * ) Notice: Subject to any disclaimer, the term of this patent is extended or adjusted under 35 U.S.C. 154(b) by 194 days.

(21) Appl. No.: 10/040,937

(22) Filed: Dec. 28, 2001

(65) Prior Publication Data

US 2002/0165462 A1 Nov. 7, 2002

Related U.S. Application Data

(60) Provisional application No. 60/304,391, filed on Jul. 9, 2001, and provisional application No. 60/259,397, filed on Dec. 29, 2000.

(51) Int. Cl.$^7$ .................................................. A61B 5/08
(52) U.S. Cl. ...................... 600/529; 600/300; 600/301; 600/323
(58) Field of Search ................................. 600/300, 301, 600/323, 324, 326, 529–543; 128/200.24, 204.18, 204.23

(56) References Cited

U.S. PATENT DOCUMENTS

| | | | |
|---|---|---|---|
| 4,407,290 A | | 10/1983 | Wilber |
| 4,796,636 A | | 1/1989 | Branstetter et al. |
| 4,802,485 A | * | 2/1989 | Bowers et al. .............. 600/324 |
| 5,036,852 A | * | 8/1991 | Leishman .................... 600/301 |
| 5,206,807 A | | 4/1993 | Hatke et al. ........... 364/413.03 |
| 5,329,931 A | * | 7/1994 | Clauson et al. ............. 600/323 |
| 5,375,607 A | * | 12/1994 | Sasagawa .................... 600/520 |
| 5,385,144 A | * | 1/1995 | Yamanishi et al. ......... 600/330 |
| 5,549,655 A | | 8/1996 | Erickson ...................... 607/42 |
| 5,591,216 A | | 1/1997 | Testerman et al. ............ 607/42 |
| 5,605,151 A | | 2/1997 | Lynn |
| 5,820,550 A | | 10/1998 | Polson et al. ................ 600/323 |
| 5,891,023 A | * | 4/1999 | Lynn .......................... 600/323 |
| 5,995,857 A | * | 11/1999 | Toomim et al. ............. 600/322 |
| 6,035,223 A | * | 3/2000 | Baker, Jr. .................... 600/323 |
| 6,045,514 A | | 4/2000 | Raviv et al. ................. 600/529 |
| 6,047,201 A | * | 4/2000 | Jackson, III ................ 600/344 |
| 6,122,535 A | * | 9/2000 | Kaestle et al. .............. 600/322 |
| 6,135,952 A | * | 10/2000 | Coetzee ....................... 600/336 |
| 6,148,814 A | * | 11/2000 | Clemmer et al. ....... 128/200.24 |
| 6,161,030 A | | 12/2000 | Levendowski et al. ..... 600/383 |
| 6,171,258 B1 | * | 1/2001 | Karakasoglu et al. ....... 600/529 |
| 6,240,316 B1 | | 5/2001 | Richmond et al. ............ 607/42 |
| 6,381,481 B1 | | 4/2002 | Levendowski et al. ..... 600/383 |
| 6,454,708 B1 | * | 9/2002 | Ferguson et al. ........... 600/300 |

FOREIGN PATENT DOCUMENTS

EP 0 743 076 11/1996

OTHER PUBLICATIONS

Davila et al., "Oximeter's Acquisition Settings Influence the Profile of the Respiratory Disturbance Index", *Sleep*, 23(2):A8–A9 (2000).

The Report of an American Academy of Sleep Medicine Task Force, "Sleep–Related Breathing Disorders in Adults: Recommendations for Syndrome Definition and Measurement Techniques in Clinical Research", *Sleep*, 22(5):667–689 (1999).

* cited by examiner

*Primary Examiner*—Mary Beth Jones
*Assistant Examiner*—Patricia C. Mallari
(74) *Attorney, Agent, or Firm*—Fulwider Patton Lee & Utecht, LLP

(57) ABSTRACT

In a technique for collecting and analyzing physiological signals to detect sleep apnea, a small light-weight physiological monitoring system, affixed to a patient's forehead, detects and records the pulse, oximetry, snoring sounds, and head position of a patient to detect a respiratory event, such as sleep apnea. The physiological monitoring system may contain several sensors including a pulse oximeter to detect oximetry and pulse rate, a microphone to detect snoring sounds, and a position sensor to detect head position. The physiological monitoring system also can contain a memory to store or record the signals monitored by the mentioned sensors and a power source. The physiological monitoring system may be held in place by a single elastic strap, thereby enabling a patient to use the system without the assistance of trained technicians.

77 Claims, 10 Drawing Sheets

SLEEP APNEA RISK EVALUATION

REFERENCE TO PRIORITY DOCUMENT

This application claims priority to U.S. Provisional Application Ser. No. 60/259,397 entitled "System and Method for Evaluating Apnea Risk" by Westbrook et al., filed Dec. 29, 2000 and U.S. Provisional Application Ser. No. 60/304,391 entitled "Sleep Apnea Risk Evaluation" by Levendowski et al., filed Jul. 9, 2001. The disclosures of these Provisional Patent Applications are hereby incorporated by reference.

STATEMENT REGARDING FEDERALLY SPONSORED RESEARCH OR DEVELOPMENT

The invention described herein was supported in part by NIH Grant HL66826-01 and HL68463-01 awarded by the National Heart, Lung and Blood Institute. The Government has certain rights in this invention.

BACKGROUND OF THE INVENTION

1. Field of the Invention

This invention relates generally to the acquisition of physiological data for health signs monitoring and, more particularly, for the diagnosis and treatment of sleep disorders.

2. Description of the Related Art

Sleep apnea (SA) is the most common disorder observed in the practice of sleep medicine and is responsible for more mortality and morbidity than any other sleep disorder. SA is characterized by recurrent failures to breathe adequately during sleep (termed apneas or hypopneas) as a result of obstructions in the upper airway.

Apnea is typically defined as a complete cessation of airflow. Hypopnea is typically defined as a reduction in airflow disproportionate to the amount of respiratory effort-expended and/or insufficient to meet the individual's metabolic needs. During an apnea or hypopnea, commonly referred to as a respiratory event, oxygen levels in the brain decrease, while the carbon dioxide ($CO_2$) levels rise, causing the sleeper to awaken. The heart beats rapidly and blood pressure rises to high levels (up to 300 mm Hg). The brief arousals to breathe are followed by a return to sleep, but the apneas may recur over 60 times per hour in severe cases.

SA is a serious, yet treatable health problem for individuals worldwide. Published reports indicate that untreated SA patients are three to five times more likely to be involved in industrial and motor vehicle accidents and have impaired vigilance and memory. Studies show that more than 15% of men and 5% of women over the age of 30 and up to 30% of men and women over the age of 65 suffer from SA. SA during pregnancy is associated with hypertension and a risk of growth retardation in the fetus. Current estimates reveal that over 90% of individuals with moderate to severe SA remain undiagnosed.

A. Polysomnography

The current "gold standard" for the diagnosis of SA is an expensive (up to $2,000) overnight sleep study, called polysomnography (PSG), that is administered and analyzed by a trained technician and reviewed by a Board Certified Sleep Specialist. The limited availability of sleep centers coupled with the high capital expense to add capacity has resulted in a growing number of patients awaiting their PSG.

i. Data Recording

A conventional full overnight PSG includes recording of the following signals: electroencephalogram (EEG), submental electromyogram (EMG), electrooculogram (EOG), respiratory airflow (oronasal flow monitors), respiratory effort (plethysmography), oxygen saturation (oximetry), electrocardiography (ECG), snoring sounds, and body position. These signals are considered the "gold standard" for the diagnosis of sleep disorders in that they offer a relatively complete collection of parameters from which respiratory events may be identified and SA may be reliably diagnosed. The RR interval, commonly referred to as beats per minute, is derived from the ECG. Body position is normally classified as: right side, left side, supine, prone, or up (or sitting erect). Typically, the microphone and the body position sensor are taped over the pharynx. Each signal provides some information to assist in the visual observation and recognition of respiratory events.

Collapse of the upper airway is identified when the amplitude of the respiratory airflow and effort signals decrease by at least 50%, snoring sounds either crescendo or cease, and oxygen desaturation occurs. A respiratory event is confirmed (i.e., desaturation not a result of artifact) by the recognition of an arousal (i.e., the person awakens to breathe), typically identified by an increase in the frequency of the EEG, an increase in heart rate, or change in snoring pattern. The remaining signals assist in determining specific types of respiratory events. For example, the EEG and EOG signals are used to determine if a respiratory event occurred in non-rapid eye movement (NREM) or rapid eye movement (REM) sleep. The position sensor is used to determine if an airway collapse occurs only or mostly in just one position (typically supine).

ii. Identifying Respiratory Events

A reduction or absence of airflow at the airway opening defines sleep-disordered breathing. Absent airflow for 10 seconds in an adult is an apnea, and airflow reduced below a certain amount is a hypopnea. Ideally one would measure actual flow with a pneumotachygraph of some sort, but in clinical practice this is impractical, and devices that are comfortable and easy to use are substituted. The most widely used are thermistors placed in front of the nose and mouth that detect heating (due to expired gas) and cooling (due to inspired air) of a thermally sensitive resistor. They provide recordings of changes in airflow, but as typically employed are not quantitative instruments. Currently available thermistors are sensitive, but frequently overestimate flow. Also, if they touch the skin, they cease being flow sensors. Measurement of expired carbon dioxide partial pressure is used in some laboratories to detect expiration, but it is not a quantitative measure of flow.

An alternative method is to measure changes in pressure in the nasal airway that occur with breathing. This approach provides an excellent reflection of true nasal flow. A simple nasal cannula attached to a pressure transducer can be used to generate a signal that resembles that obtained with a pneumotachygraph. It allows detection of the characteristic plateau of pressure due to inspiratory flow limitation that occurs in subtle obstructive hypopneas.

An obstructive apnea or hypopnea is defined as an absence or reduction in airflow, in spite of continued effort to breathe, due to obstruction in the upper airway. Typical polysomnography includes some recording of respiratory effort. The most accurate measure of effort is a change in pleural pressure as reflected by an esophageal pressure monitor. Progressively more negative pleural pressure swings leading to an arousal have been used to define a "Respiratory Effort Related Arousal" (RERA), the event associated with the so-called "Upper Airway Resistance Syndrome". However the technology of measuring esophageal pressure is uncomfortable and expensive, and rarely used clinically. Most estimates of respiratory effort during polysomnography depend on measures of rib cage and/or abdominal motion. The methods include inductance or impedance plethysmography, or simple strain gages. Properly used and calibrated, any of these devices can provide quantitative estimates of lung volume change and abdominal-rib cage paradox. However calibrating these devices and keeping them accurately calibrated during an overnight recording is very difficult and as a practical matter is almost never done. Thus the signals provided by respiratory system motion monitors are typically just qualitative estimates of respiratory effort.

B. Measuring Oxyhemoglobin Desaturation during Sleep

One of the functions of the lungs is to maintain a normal partial pressure (tension) of oxygen and carbon dioxide in the arterial blood. Various dynamic processes, such as ventilation, diffusion, and the matching of ventilation and perfusion within the lung support this function. Ventilation or breathing, for example, continuously replenishes the oxygen ($O_2$) in the gas-exchanging units of the lung, the alveoli, and removes carbon dioxide ($CO_2$). An apnea or hypopnea occurring during sleep, however, temporarily decreases alveolar ventilation, causing a drop in arterial oxygen tension ($pO_2$) and an increase in arterial carbon dioxide tension ($pCO_2$). Because there is currently no accurate non-invasive method for continuously monitoring arterial $pO_2$ or $pCO_2$, non-invasive measures of oxyhemoglobin percent saturation are instead used today to determine apneas or hypopneas.

Blood transports oxygen both as dissolved $O_2$ and in chemical combination with hemoglobin. The amount of dissolved $O_2$ is directly proportional to the partial pressure of $O_2$. At atmospheric pressure, the amount of dissolved $O_2$ accounts for only a trivial amount of the blood oxygen content, not nearly enough to sustain life. Each gram of hemoglobin can carry up to 1.34 ml of $O_2$. Oxyhemoglobin percent saturation (saturation) is the ratio of the amount of $O_2$ actually combined with hemoglobin in the red blood cells to the maximum capacity of that hemoglobin to bind $O_2$, expressed as a percent. At sea level, a healthy person typically has a $pO_2$ of about 100 mmHg and saturation between 97% and 98%, or on average 97.4%.

The amount of $O_2$ combined with hemoglobin is not linearly related to $O_2$ tension, $pO_2$. A graph of saturation against $pO_2$ is a sigmoid curve that has a steep slope between a $pO_2$ of 10 and 50 mmHg, and a very flat portion between 70 and 100 mmHg. The relationship between saturation and $pO_2$ at the top of the curve is optimal for getting oxygen from the lungs to the tissue, but makes detecting small drops in arterial $pO_2$ difficult. When oximetry is used to identify decreases in ventilation occurring as the result of upper airway collapse in persons with sleep apnea, the non-linear characteristics of the curve are particularly relevant. This is because desaturations resulting from sleep apnea occur most frequently in the range between 88% and 98%, the flat portion of the curve. The American Academy of Sleep Medicine Task Force recently established one of the main criteria for identifying a sleep apnea/hypopnea: desaturation>3% lasting a minimum of 10 seconds. See the Report of the American Academy of Sleep Medicine Task Force: Sleep-Related Breathing Disorders in Adults: Recommendations for Syndrome Definition and Measurement Techniques in Clinical Research, Sleep, Vol. 22, No. 5, 1999. It might be said that this report reflects a pessimistic view of the accuracy of the usual pulse oximetry, not physiology.

Defining a respiratory event by a fixed change in saturation without defining the starting saturation, however, does not make biological sense. For example, a 3% fall in saturation from 98% is a drop in pO2 of 38 mmHg, while a 3% decrease from 94% reflects a 9-mmHg $pO_2$ change.

C. Oximetry

The measurement of oxyhemoglobin saturation using pulse oximetry was developed in the 1940s, but became practical and universally available with the availability of microprocessors. A pulse oximeter typically utilizes two different light sources (e.g., red and infrared), which measure different absorption or reflection characteristics for oxyhemoglobin (i.e., the red, saturated blood) and deoxyhemoglobin (the blue, unsaturated blood). The oximeter then measures the ratio (percent) of saturated to unsaturated hemoglobin. One method to determine blood oxygen saturation is by transmission oximetry. Devices utilizing transmission oximetry operate by transmitting light through an appendage, such as a finger or an earlobe, and comparing the characteristics of the light transmitted into one side of the appendage with that detected on the opposite side. Another method to determine blood oxygen saturation is by reflectance oximetry, which uses reflected light to measure blood oxygen saturation. Reflectance oximetry is useful to measure oxygen saturation in areas of the patient's body that are not well suited for transmission measurement. See, for example, the description in U.S. Pat. No. 4,796,636 to Branstetter and Edgar.

Pulse-oximeter devices commonly used for the diagnosis of sleep apnea were originally designed to monitor patients in critical care conditions, even though the requirement for optimal sensitivity for the two applications differs. In critical care monitoring, the device is typically calibrated to set off an alarm and notify hospital staff when a patient's saturation falls below a certain critical threshold (e.g., 88%). Averaging the data across a wider time window (e.g., five seconds) is a common technique embedded in the device to minimize false alarms due to measurement artifacts. Studies have shown that the sensitivity of a pulse-oximeter to subtle fluctuations in oxygen saturation due to partial obstruction of the pharynx is directly related to the averaging window that is employed. See, for example, "Oximeter's Acquisition Settings Influence the Profile of the Respiratory Disturbance Index" by Davila D, et al. in Sleep 2000: 23; Abstract Supplement 2 at A8–A9. A calibration curve developed to optimize the accuracy of the oxygen saturation measurements across the typical specified range (i.e., from 100 to 70%), a requirement in critical care situations, may reduce the accuracy of the measures at more subtle resolutions (e.g., 98.0 to 97.5%). In monitoring a sleeping person, however, a repetitive pattern of oxygen desaturation between 98% and 96% that is terminated by an arousal is significant, though commonly overlooked due to the insensitivity of existing devices.

Most commercial pulse-oximetry sensors in use today are designed to be taped or affixed to the body with a wire lead that is inserted into the pulse-oximeter monitoring equipment. This wire lead, however, is one of the main sources of measurement artifacts. During sleep, the wire can get caught in the patient's bedding, thus causing a disruption of the sensor contact with the skin, where the red and infrared light sources are being measured. Furthermore, in many conventional in-home systems used to determine or treat apnea, the patient is required to apply sensors, plug in wires, apply and adjust transducers, straps, gauges, or other measurement devices, or operate a computer-controlled bedside unit. This equipment can be difficult for a lay person to apply and properly operate. Thus, a device that eliminates or reduces the use of wires, and can be reliably self-applied with minimal instruction would be beneficial in the accurate diagnosis of sleep disorders.

D. Continuous Positive Airway Pressure (CPAP)

Sleep apnea treatment is widely available and relatively inexpensive. Patients can be fitted with a Continuous Positive Airway Pressure (CPAP) device, which delivers air at a constant increased pressure via a nasal mask worn throughout the night. This increased pressure propagates through the nose into the pharynx and prevents the airway from collapsing.

CPAP is the most common treatment for obstructive sleep apnea (OSA). OSA is characterized by frequent periods of airway occlusion during sleep, with concomitant obstruction of inspiratory airflow, drop in blood oxygen, and interruption of sleep when the patient awakes to use voluntary muscle contraction to open the airway and take a few deep breaths. Typically a patient diagnosed with clinically important sleep apnea/hypopnea will undergo a CPAP titration and trial during attended PSG. A technician assists the patient with the fitting of the CPAP mask and determines the pressure required to keep that patient's airway open during sleep. Recent developments in CPAP technology include auto-titration units, which automatically adjust the pressure to that required at any particular time during sleep. These auto-titration CPAP units, however, are more expensive than standard CPAP devices and not usually reimbursed by medical insurance. Their application is generally limited to unattended automatic determination of required pressure, rather than relying on a technician to determine the pressure needed during PSG.

Some states, including Alabama, require employers to monitor the compliance of CPAP use for truck drivers diagnosed with sleep apnea. A recent innovation of the CPAP technology includes a "smart system" to monitor compliance by recording and storing the time the CPAP device is on at the prescribed pressure. A way to inexpensively monitor treatment outcomes, improve the titration of CPAP devices, and improve compliance is thus desirable.

E. Neuromuscular Stimulation

A number of recent developments in the area of treating sleep apnea suggest that neuromuscular stimulation may be appropriate for the treatment of sleep apnea. See, for example, U.S. Pat. No. 6,240,316 to Richmond and Loeb (hereinafter referred to as Pat. '316), U.S. Pat. No. 5,549,655 issued to Erickson (hereinafter referred to as Pat. '655), and U.S. Pat. No. 5,291,216 (hereinafter referred to as Pat. '216). One of the preferred embodiments described by Pat. '316 and '655 includes an open loop system, whereby stimulation is timed to the patient's respiration. Pat. '316 describes a method for sensing obstructed airway passage by sensing airway pressure, characteristic snoring sounds, mechanical motion, or muscle activity. Pat. '655 describes stimulation of the upper airway using a measurement of respiratory effort. Pat. '216, on the other-hand, describes that the placement of the neuro-stimulation electrode may be sufficient to maintain upper airway passage. More effective treatment of sleep apnea could be provided if improved detection of sleep apnea events were coupled with the delivery of stimuli provided by such neuromuscular devices.

From the discussion above, it should be apparent that there is a need for a more efficient, inexpensive, and accurate way to collect physiological data to detect sleep related obstructive respiratory events, as well as address the difficulties and problems discussed above. The present invention fulfills these needs.

SUMMARY OF TILE INVENTION

The present invention provides a technique to collect and analyze physiological signals or data for the diagnosis or treatment of sleep apnea. A sleep apnea risk evaluation system constructed in accordance with the present invention unobtrusively collects data during sleep such that the collected data may be analyzed to detect respiratory events indicative of a sleep apnea condition. The patient may then be assigned an overall risk for obstructive sleep apnea based on the collected data and the patient's known prior probability of risk for sleep apnea. The prior probability of risk may be determined, for example, by means of a patient questionnaire.

A sleep apnea risk evaluation system constructed in accordance with the present invention has several unique features when compared to known commercially available systems designed to acquire signals for the detection of sleep apnea, particularly in the home. These distinguishing characteristics include the acquisition and recording of all of the signals or data needed to detect clinically important abnormal respiratory events associated with the sleep apnea syndrome using a small, lightweight, self-powered physiological monitoring system that is applied to the forehead and held in place with a convenient single elastic strap. The physiological monitoring system thereby eliminates all wire leads between the patient and a data recorder. Thus, in contrast to existing apnea risk evaluation systems, the patient is not required to apply individual sensors, plug in wires, apply and adjust transducers, straps, gauges, or other measurement devices, or operate a computer-controlled bedside unit. Methods developed for the physiological monitoring system improve the accuracy and resolution of the detection of oxyhemoglobin desaturation events caused by sleep apneas or hypopneas. The methods developed to detect respiratory events may also be implemented off-line or in real time. In this way, physiological data may be more easily and efficiently collected for more accurate detection of sleep related obstructive airway events.

In one embodiment, a physiological monitoring system constructed in accordance with the invention includes a small, light-weight monitor device that affixes to a patient's forehead and incorporates several patient physiological sensors, including a pulse oximeter to detect oximetry and pulse rate, a microphone to detect snoring sounds, and a position sensor to detect patient head position. In an alternative embodiment, the system may be modified to measure airflow with a thermistor or a plastic cannula running from the enclosure across the bridge of the patient's nose to the nares. The monitor device preferably contains a power source and memory to store or record the monitored signals and data. The physiological monitor device is preferably held in place by an unobtrusive mechanism, such as a single elastic strap, that enables the patient to use the physiological monitor system without the assistance of trained technicians. A calibration curve fitted for the physiological monitor device focuses on accurate measurements at 0.5% increments between 100% and 80% oximetry levels, thereby improving the detection of sleep apnea.

The physiological monitoring system may be integrated with other therapeutic devices, such as a Continuous Positive Airway Pressure (CPAP) device. The physiological monitoring system thereby provides data on the efficacy and the time of use of a therapeutic device, such as the CPAP device. The physiological monitoring system may also contain additional sensors or may use the same sensors to monitor other physiological signals, such as ocular movement or heart rate. The physiological monitoring system may also interface or be integrated with a neuromuscular stimulation device, thereby eliminating the need for an external controller device, e.g., a bedside controller.

If the physiological monitoring system is to be used for monitoring $SpO_2$ in patients in real-time, a digital display LCD can be incorporated into the monitoring device to present the $SpO_2$ values to the patient. Alternatively, a low-powered radio frequency transmitter can be used to provide wireless transmission between the monitor device attached to the patient's forehead and a bedside unit that displays the $SpO_2$ results. In either of these real-time applications, the need for onboard memory will be reduced or eliminated.

Other features and advantages of the present invention should be apparent from the following description of the preferred embodiment, which illustrates, by way of example, the principles of the invention.

DETAILED DESCRIPTION

Figure 1:
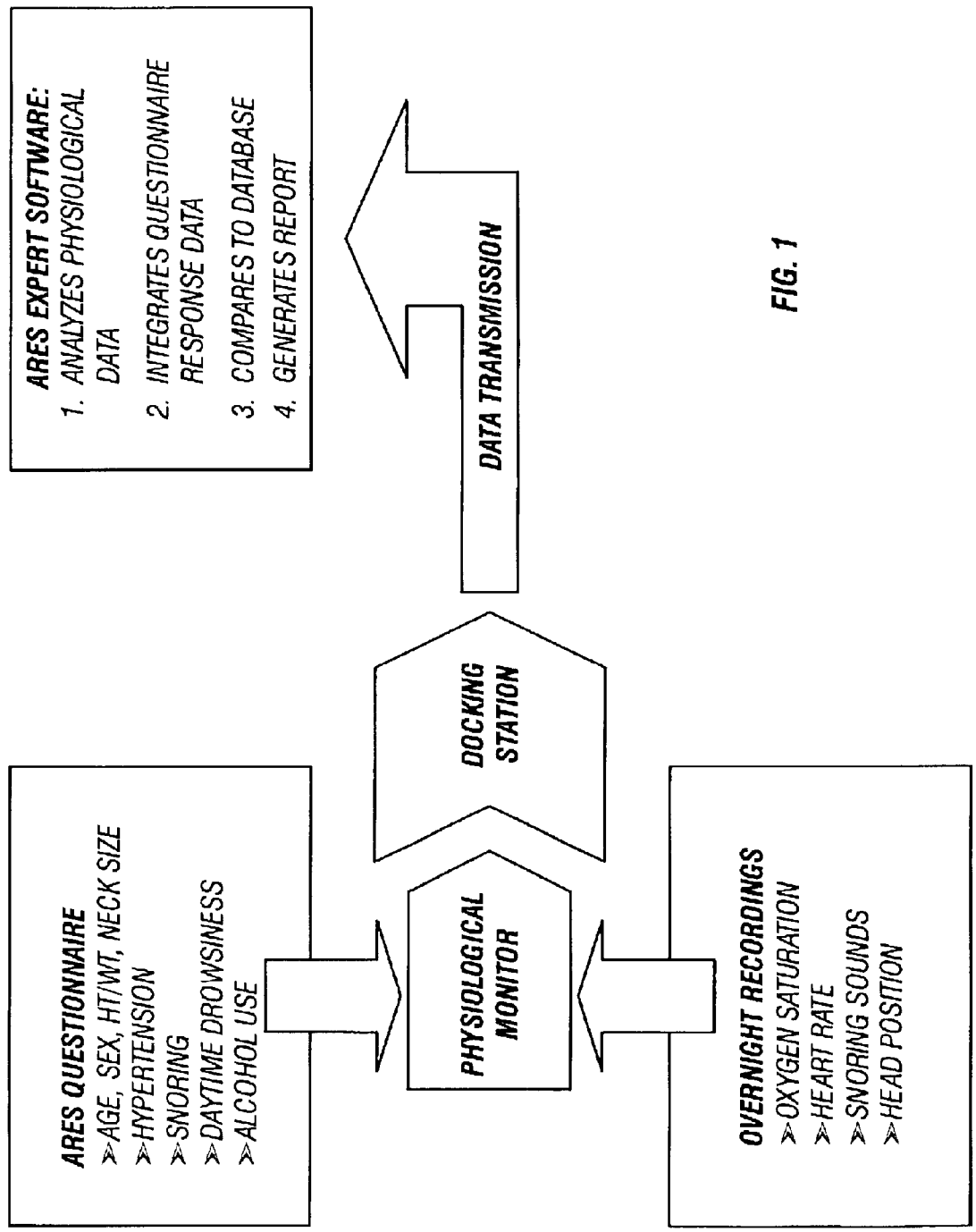
FIG. 1 is block diagram of the data acquisition and analysis subsystems for evaluating apnea risk constructed according to the present invention.

As indicated above, a monitoring system constructed in accordance with the present invention provides a device that reliably detects a patient's sleep apnea condition without excessive intrusion into the patient's sleep experience. FIG. 1 shows a block diagram of the mechanisms for collecting data and evaluating risk for sleep apnea, in accordance with the invention. As indicated in FIG. 1, the preferred embodiment includes an Apnea Risk Evaluation System (ARES) questionnaire that is filled out by a sleep study patient. Those skilled in the art will be familiar with the questions that are posed to patients being evaluated for sleep apnea, and will be able to construct such a questionnaire without further explanation. The questionnaire thereby provides information that can be submitted to discriminant function or other type of analysis that can be used to assign risk categories based on questionnaire responses. In addition to patient responses elicited by the questionnaire, overnight recordings are employed to collect patient physiological data during a session of the patient's sleep. The patient physiological data collection and recording occurs automatically through a physiological monitoring system.

The recorded data may be transferred to a computing system for analysis, such as may be implemented through a Personal Computer that is running at a network docking station or through a similar computing system that supports data transfer from the physiological monitoring system to a computer system that contains ARES expert software. In this description, it should be understood that references to computing devices, computing systems, and the like, are not intended to refer to specific configurations of computing machinery. Rather, it should be understood that references to computer systems and computing devices are intended to refer to any configuration of processors that may receive data as input, perform operations on data, and produce output that is suitable for the requisite functionality. Thus, "computer systems" and "computing devices" may include Personal Computer workstations, mainframe computers, hand-held computing devices, integrated circuit chips for data processing, and the like, alone or in combination, depending on the operations to be performed and the output to be produced.

The apnea risk evaluation system may analyze the collected data in conjunction with the ARES questionnaire results to compare findings against a sleep apnea database, thereby operating as an expert system, and may generate a report of the patient's risk for sleep apnea. The sleep apnea database preferably contains physiological sleep data from at least one person who is classified as suffering from sleep apnea and from at least one person who is not suffering from sleep apnea (the "control"). The computing system that receives the overnight physiological recordings and the ARES Expert Software computing system may comprise the same Personal Computer, which then generates the sleep apnea risk report, or may comprise independently operating computer systems or other distributed processing configurations, any one of which may have responsibility for generating the sleep apnea risk report.

Figure 2:
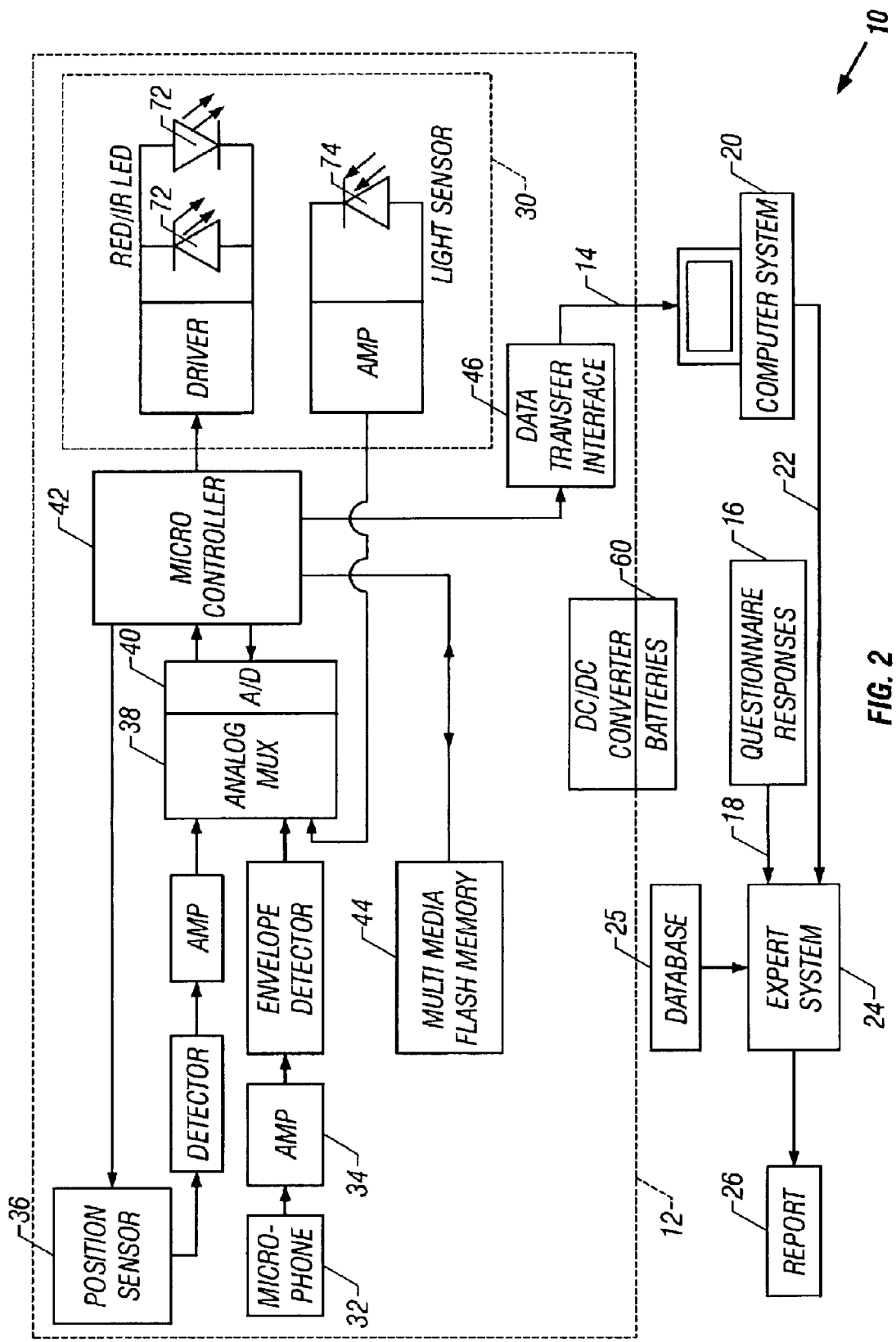
FIG. 2 is a functional diagram of the system for evaluating apnea risk constructed according to the present invention.
Figure 3:
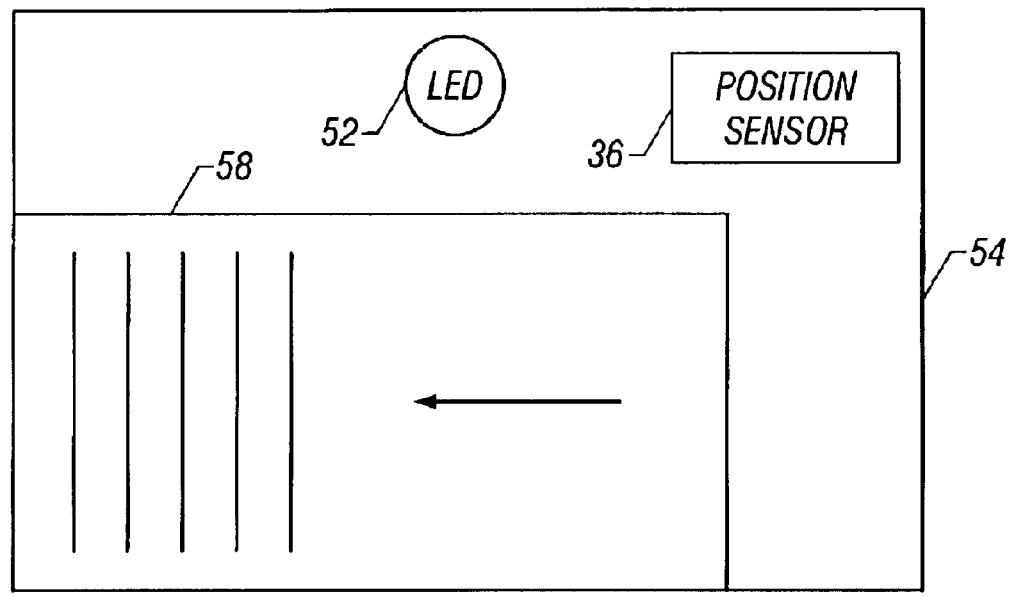
FIG. 3 is a top view of a physiological monitor device of the apnea risk evaluation system shown in FIG. 2.
Figure 4:
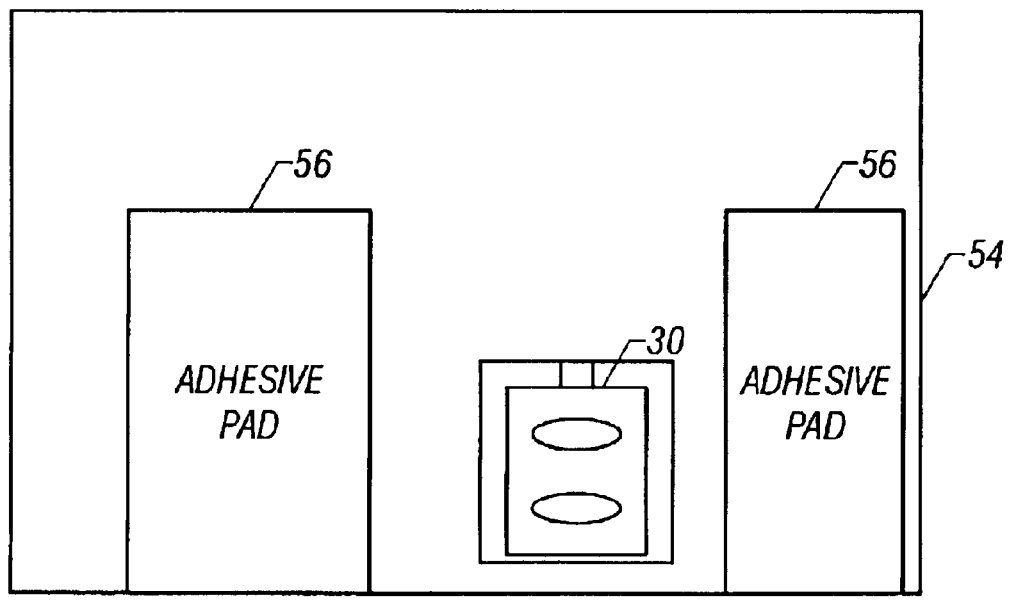
FIG. 4 is a bottom view of the physiological monitor device shown in FIG. 2.

FIG. 2 of the accompanying drawings shows an apnea risk evaluation system 10 constructed in accordance with a preferred embodiment of the present invention, used for evaluating sleep apnea risk. The system 10 includes (a) a physiological monitoring system 12 for continuously monitoring a plurality of an individual patient's physiological parameters during sleep and for generating physiological parameter signals 14 representing the plurality of the individual's physiological parameters; (b) a computer system 20 that recognizes and quantifies abnormal respiratory events from the physiological parameter signals 14 and generates secondary, respiratory event signals 22 representing the recognition and quantification of such respiratory events; and (c) an expert system 24 that (i) utilizes data comprising patient responses from a standardized questionnaire 16 with which anthropomorphic and clinical information 18 are obtained from the individual such that risk factors are entered into the system, (ii) the respiratory event signals, and (iii) a database of physiological data from sleep apnea patients and controls, to generate a report 26 concerning levels of potential risk for sleep apnea for the individual patient under study.

1. The Physiological Monitoring System

Referring to FIGS. 2–8, the physiological monitoring system 12 is shown as including a low-powered lightweight monitor device 30 that incorporates the necessary pulse oximetry ($SpO_2$) sensor components, such as sensors, amplifiers, filtering, and the like. The system 12 also includes a microphone 32 that records snoring and breathing sounds, an amplifier 34, and a patient sensor 36, such as an accelerometer or a two-axis position sensor that responds to changes in patient position and movement, combined with an analog multiplexer (MUX) 38 that receives the various sensor signals, an analog-to-digital (A/D) converter 40 that digitizes the sensor signals, and a micro-controller 42 that controls the pulse oximetry sensor and also receives and transmits the digitized sensor signals for the individual patient's physiological parameters. The micro-controller has an associated flash memory 44, such as a multi-media flash memory card, capable of storing forty hours of sleep data, and a high-speed data transfer connection 46 to a multi-media flash card reader or an RS-232 serial interface for uploading and downloading data to and from the physiological monitoring system 12 to a host computer system 20, an on/off switch 50, and an LED diode 52 for indicating operation status of the physiological monitoring system.

FIGS. 3–6 illustrate an electromechanical layout of a self-powered physiological monitoring system 12 for use in the apnea risk evaluation system 10. All of the physiological monitoring system components are preferably mounted on a multi-layered printed circuit board 62 (FIG. 6) fitted inside an enclosure 54, which can be attached to the patient's body with an adjustable strap. The preferred embodiment attaches the physiological monitoring system to the patient's forehead, but other locations of the patient's body may be used, so long as sufficient skin surface is available for the pulse oximetry sensor components to properly function.

Among the advantages provided by this system 12, compared to other monitoring devices for similar purposes: (a) its forehead location and low weight, for less intrusion into a patient's sleep experience, (b) all components of the physiological monitoring system are combined in a single small enclosure, which increases reliability and reduces inhibition of patient movement during the sleep study, (c) low power consumption that allows the use of battery power, thereby eliminating the problems associated with external power cords, and (d) ease of self-application. The bottom of the enclosure 54 is preferably slightly concave to conform to the shape of the patient's forehead. In the preferred embodiment, an elastic headband 73 (shown in FIGS. 7 and 8) is used to assist in maintaining the physiological monitoring system in place during sleep.

Alternatively, two hydrogel/adhesive strips 56, applied to the bottom of the enclosure 54, can be used to secure the physiological monitor to the patient's forehead. A 1.0 cm thick foam enclosure pad 80 (see FIG. 8) can be applied to the bottom of the enclosure as a comfortable interface between the physiological monitoring system and the patient's forehead. The enclosure pad 80 further improves signal accuracy by surrounding the $SpO_2$ oximetry sensor 30 and shielding it from ambient light. A foam stabilizing pad 81 is placed behind the $SpO_2$ sensor to apply direct pressure against the forehead (see FIG. 8). This design allows the physiological monitoring system to remain comfortably in place while applying approximately 100 mm Hg of constant pressure on the $SpO_2$ sensor against the patient's forehead to minimize skin movement beneath the sensor and maximize signal quality while recording.

Figure 5:
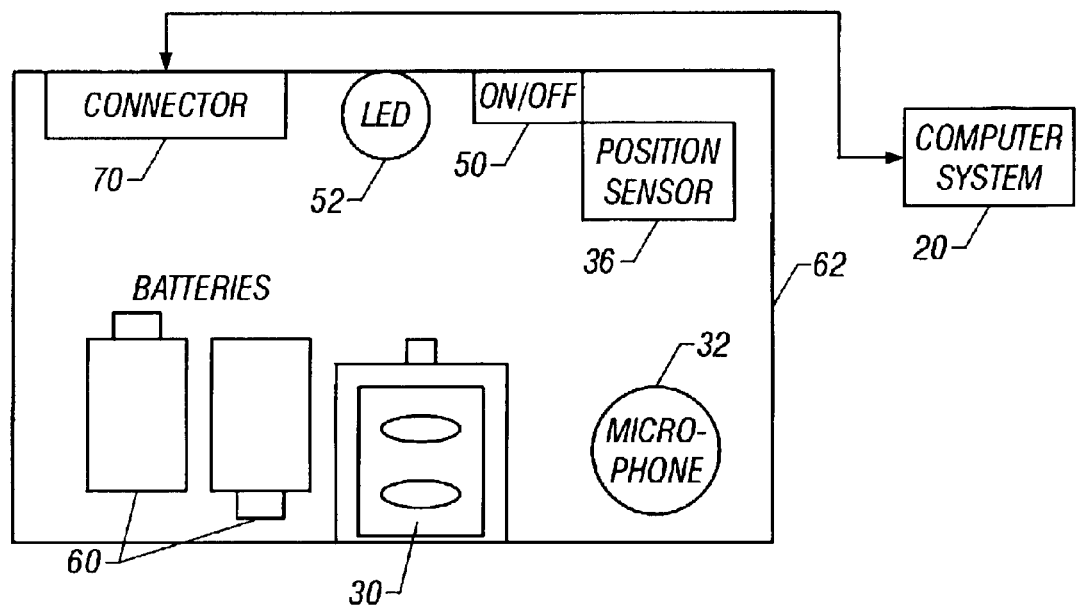
FIG. 5 is a top view of a PC board of the physiological monitor device of FIG. 2.
Figure 6:
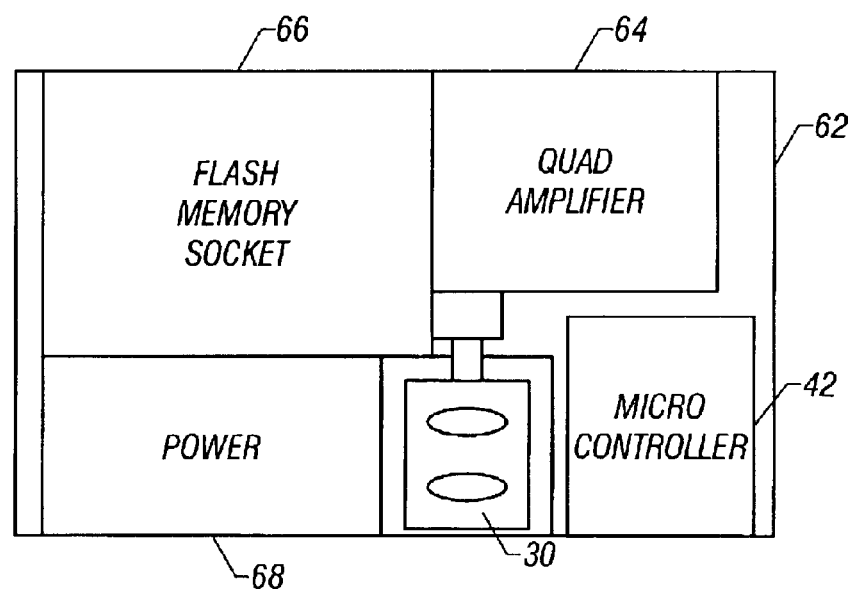
FIG. 6 is a bottom view of the PC board of FIG. 4.
Figure 7:
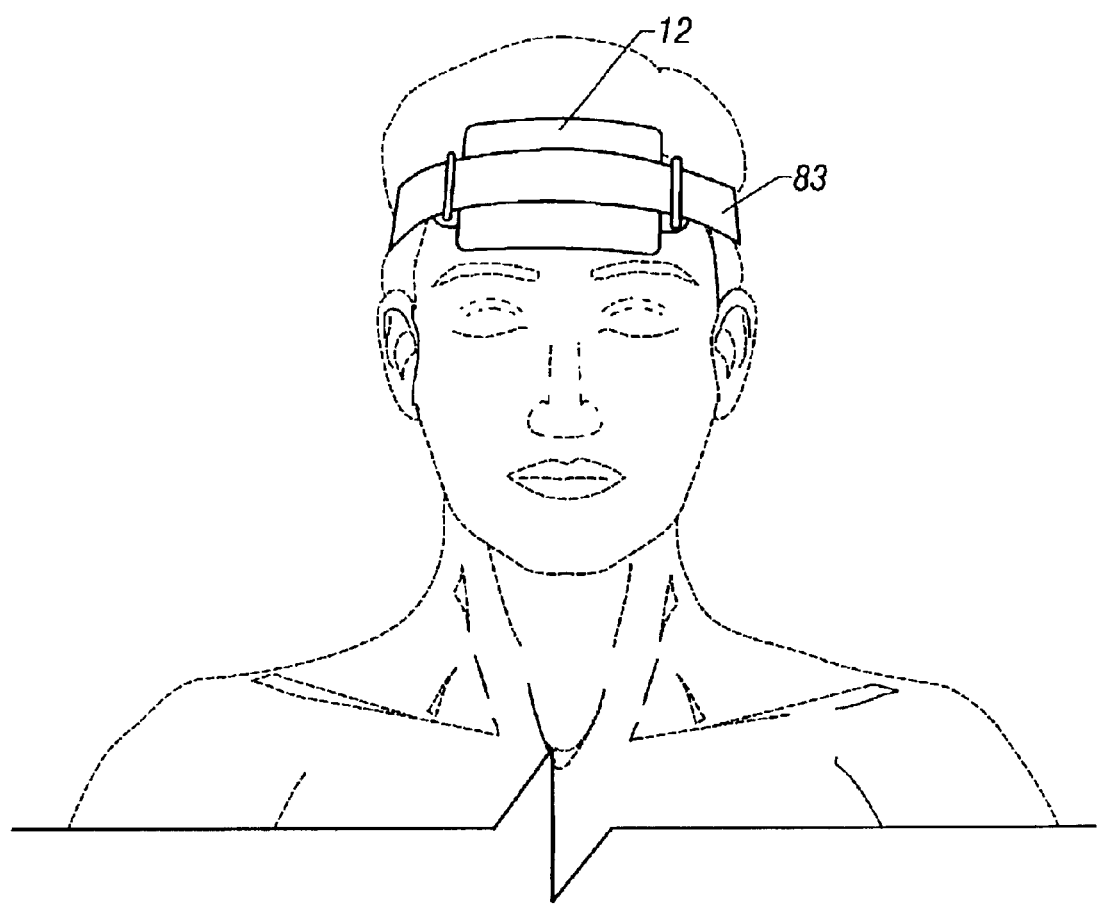
FIG. 7 shows the physiological monitor device of FIG. 2 affixed on a patient's forehead.
Figure 8:
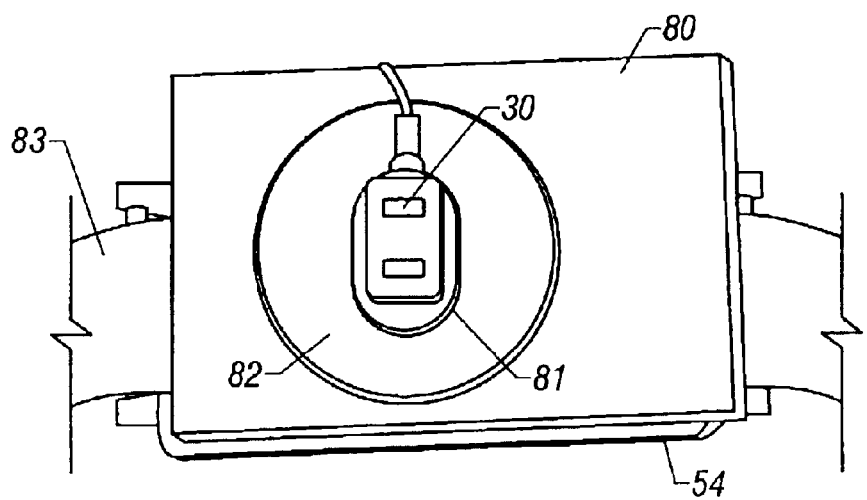
FIG. 8 shows the back side (with foam pad) of the physiological monitor device of FIG. 2.

In one embodiment of the invention, rechargeable batteries are mounted inside the enclosure 54, and a cable jack is affixed to the enclosure body and circuitry mounted on the PC board 62, to provide the capability to recharge the batteries. Alternatively, the top or lid 58 of the enclosure 54 can be removed to replace a disposable battery 60. Two rechargeable N-type nickel-metal hydride batteries 60 are selected for the preferred configuration due to size, weight, commercial availability, and their capability to provide sufficient capacity to power data acquisition for approximately nine hours. Other types of disposable or rechargeable batteries may also be used, provided that the size and weight of the batteries does not preclude the physiological monitoring system from being comfortable on the patient while high quality data signals are acquired. The PC board 62 of the physiological monitoring system, as illustrated in FIGS. 5 and 6, includes circuitry 64 for the amplifier and passive components, a socket 66 for the flash memory, a power supply 68, and a connector 70 such as an 8-pin connector, for connection to the computer system 20, if necessary.

In an alternative embodiment, the physiological monitoring circuitry is enclosed and affixed near the crown of the patient's head. A short lead from the enclosure permits relatively easy and unobtrusive affixing of the pulse-oximetry sensor and microphone to the forehead by the patient. Affixing the enclosure near the crown of the head is important, because this location and the forehead are the only two placements that would not impede sleeping in all regular body positions.

A. $SpO_2$ Sensor

A finger pulse oximeter sensor is typically utilized with commercially available equipment used for sleep studies to acquire pulse ate and oximetry readings of blood oxygen saturation. In accordance with the present invention, however, the system 10 utilizes a physiological monitor 12 having a pulse oximeter ($SpO_2$) sensor affixed to the patient's forehead to acquire pulse and oximetry readings. Forehead oximetry is sometimes applied in surgical, critical care, emergency room, and other clinical care applications, but its use has not been reported in sleep studies. One reason currently available forehead sensors used in clinical applications are not ideally suited for sleep studies is that the external wires that connect to the micro-controller and data recorder cause movement of the sensor, resulting in measurement artifacts that cause inaccuracy. In the novel system 10, the forehead sensor 30, micro-controller 42, and the recorder (i.e., the flash memory 44) are incorporated into the physiological monitoring system, thus eliminating these wire leads, and such problems are solved.

Circuitry of the physiological monitoring system 12 has been designed to provide correct excitation for the LED's and light sensors, power to the sensors, and amplify and filter the signals with a sampling rate, for example, of 100 samples/sec. The methods used to amplify the AC components of the red and infrared signals, compute the raw $SpO_2$ values, and smooth the data are described in greater detail below. To optimize the accuracy and reliability of the signal input, the $SpO_2$ sensor is offset from the enclosure center to position it near a supra-orbital artery of the patient. In the preferred embodiment, the physiological monitoring system 12 affixed on the forehead may be held on the patient with a single elastic strap around the head. As noted above, conventional sleep study equipment uses finger pulse oximetry sensors. The physiological monitoring system 12 constructed in accordance with the present invention utilizes an oximetry sensor that is affixed to the patient's forehead, preferably a reflectance-type sensor. Although reflectance sensors have been available for approximately ten years, the inventors have not found any reputable studies that report use of a reflectance sensor affixed to a patient's forehead in the study of sleep-disordered breathing.

The inventors of the present invention have found that placement of the pulse oximetry sensor at the patient's forehead reduces the time it takes to recognize desaturation events, apparently because the forehead is closer to the heart than the finger (see Belozeroff et al., cited above). A finger sensor typically exhibits a ten-second delay in the recognition of the onset of a respiratory event. This delay is in part a result of the time it takes for the blood to be pumped from the lungs to the finger. The delay in the detection of desaturations can be greater than ten seconds, depending on the averaging window used by the pulse-oximeter device. The inventors conducted a comparison study of finger vs. forehead sensor placement using identical pulse-oximetry equipment and have found a consistent delay in the recognition of the onset and recovery of a desaturation event by an average of five seconds per event. A reduction in the time delay in recognizing the onset of a desaturation event improves the detection of respiratory events because it increases the correlation in the time domain between the oximetry values and the other signals used to recognize respiratory events.

B. Microphone

A small microphone 32 is included in the physiological monitoring system 12, directed towards the patient's pharynx, for acquisition of a signal indicating snoring intensity. The microphone 32 is preferably located at the bottom of the physiological monitor system, providing a novel location, i.e., its placement is at a constant distance from the pharynx. In conventional sleep studies, a microphone is taped over the pharynx, such that the sounds made by the patient can be muffled or distorted by bedding or by excessive body fat. The microphone position of the preferred embodiment maximizes the signal input from the patient while minimizing cross talk that might otherwise be acquired from a snoring bed partner.

C. Head Position and Movement Sensor

Accelerometer-, capacitance- or resistance-based technologies can be used to detect times when the patient's head is in the upright, supine, or to the left or right lateral positions, as well as to detect patient head movement generally. A head position monitor 36 is a better indicator of pharynx position than the trunk position monitors typically used in sleep studies. It is pharynx or neck position that most influences the collapsibility of the upper airway. Detection of head movement may be useful in detecting respiratory event related arousals. In the preferred embodiment, an accelerometer 36 is used, since it is substantially smaller than a fluid and capacitor-based X-by-Y position sensor (approximately 5 mm (L)×5 mm (W)×2 mm (H) vs. 10 mm diameter×15 mm height, respectively). In order to identify the standard head positions listed above, a minimum of one position sensor is required. If increased spatial resolution is required, two position sensors could be mounted in the enclosure on opposite axes (i.e., vertical and horizontal).

D. Micro-Controller

In a preferred embodiment, the micro-controller 42, analog to digital (A/D) converter 40, and multiplexer 38 are combined in a single integrated circuit chip that is used to sequence and digitize the analog signals. In an alternative embodiment, separate chips for the micro-controller, A/D converter, and multiplexer can be used to sequence and digitize the analog signals. Compared to an integrating A/D converter, an A/D converter that utilizes a successive approximation conversion is preferable because a successive approximation A/D converter provides substantially faster conversion processing and decreases power consumption by a factor of approximately five to ten. The micro-controller chip is programmed to control signal acquisition and digitization, store the data to flash memory and control the data transfer interface 46 for uploading data to or downloading data from the flash memory. Because the most power consuming components of the physiological monitor are the $SPO_2$ sensor red and infrared LEDs 72, the micro-controller is programmed to periodically excite them for just a sufficient period of time for the light sensor 74 and A/D converter to acquire the sample.

E. Memory

In the preferred embodiment, the physiological signals needed to provide a full-disclosure recording are stored in memory. Alternatively, the micro-controller can be programmed to perform some pre-processing so that a more limited amount of data are stored. Flash memory chips 44 provide a low cost method to store the signals acquired during use of the physiological monitor 12. In the preferred embodiment, a removable flash card such as a multi-media flash card is used to provide greater flexibility and reduce costs. Flash cards with 8 MB, 16 MB, 32 MB, or 64 MB capacity can be inserted into the same socket depending on the number of nights of data to be acquired. A 32 MB flash card, for example, should have sufficient storage capacity to store the signals acquired during three sessions of sleep recordings. Alternatively, the signals may be stored on a flash chip or any nonvolatile low powered memory of equivalent storage capability.

F. Data Transfer

Figure 9:
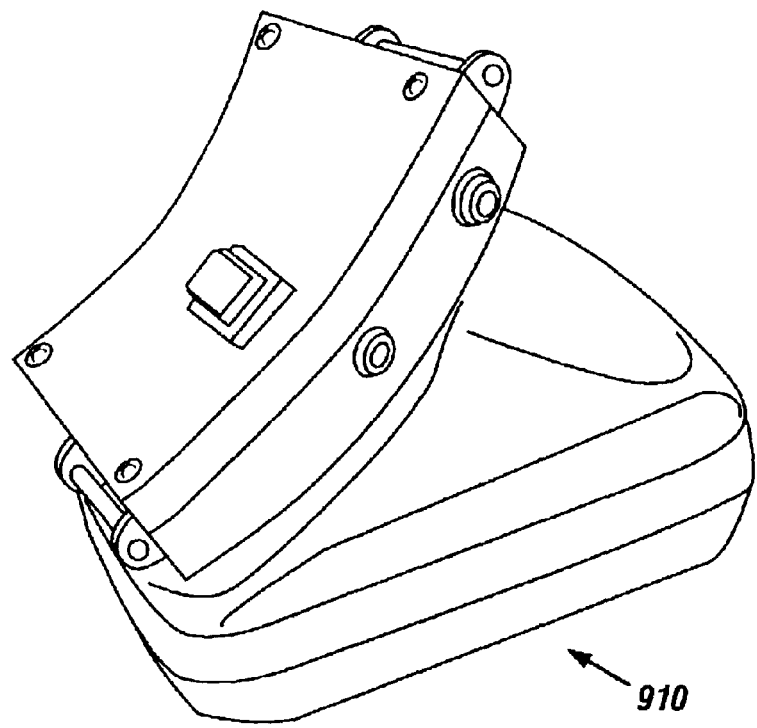
FIG. 9 shows the physiological monitor device placed in a docking station as signals or data recorded by the physiological monitor device are downloaded to a computer system.

When a multi-media flash card is utilized, a multi-media flash card reader provides the optimal data transfer capability. In the preferred embodiment of the system 10, the physiological monitor 12 may interface with a docking station 910, such as illustrated in FIG. 9, for data transfer. The docking station preferably includes a multi-media flash card reader and network or communication card, which may be used to download the data from the flash memory to an external component, such as the computer 20 within the system 10 or to a computer networked to the system computer. The docking station 910 may also include battery-recharging circuitry so that the batteries in the physiological monitoring system will automatically charge whenever it is seated in the docking station.

If the docking station 910 is configured with a wireless telephone link, data may be directly transmitted to an offsite facility for processing and report generation. A docking station with wireless telephone link would also allow the physiological monitor firmware to be remotely upgraded. The physiological monitoring system 12 may also communicate (e.g., upload and download data) directly with the computer system 20 through a wireless interface that enables wireless communication in an efficient manner (e.g., RF link or Blue-tooth protocol). As an alternative, a custom-made PC board can be used to connect the physiological recorder, via the connector 70, to a commercially available flash card reader. Commercially available flash card readers connect directly to a host PC via a USB connection or the parallel port. In a third embodiment, a high-speed RS-232 serial interface circuitry 46 can be incorporated into the physiological monitor 12 to upload and download data to and from the flash memory to a computer 20 using a standard serial data cable. The serial interface circuitry is preferably incorporated into an adapter cable, rather than on the physiological monitor PC board, to reduce size and weight. The serial adapter circuitry is enclosed in a cable harness with a standard nine-pin serial connection on the opposite end (to be inserted into a computer). This cable enables data to be uploaded to and downloaded from the flash card.

G. Power Supply/Battery

In the preferred embodiment, two N-type nickel-metal hydride batteries 60 are mounted inside the enclosure. With a capacity of 360 milliamps per hour, currently available N-type batteries provide up to nine hours of use. Alternatively, two rechargeable size AAA batteries may be affixed inside the enclosure. Two size AAA batteries should provide sufficient capacity to power the physiological recorder for a minimum of approximately 14 hours. The same jack and circuitry inside the enclosure can be used to recharge nickel-cadmium and nickel-metal hydride batteries without removal. To minimize the weight of the physiological monitor (which must be maintained in position on the forehead), the two AAA batteries can be inserted into a separate enclosure, with a wire leading from the battery enclosure to the physiological monitor. However, if the wire were to become tangled during sleep, this approach might compromise comfort and signal quality. Rechargeable lithium batteries can also be used, however, a protective recharging circuit must be added.

H. Functionality Indicator

In the preferred embodiment, LED diodes 52 are positioned so that the patient/user can observe them when looking into a mirror. The LEDs can be used as an on/off indicator and to notify the patient when the SpO$_2$ sensor is optimally positioned. In the preferred embodiment, a dual colored LED diode 52 is used, however, a single or multiple LED diodes could be used. As soon as the physiological monitor is turned on, the first LED (LED #1) is illuminated in a steady state. While the micro-controller is calibrating the SpO$_2$ measuring circuit and assessing the quality of the SpO$_2$ signal, the second LED (LED #2) may blink rapidly. LED #2 is changed to a steady state once an acceptable signal quality is obtained. As long as an acceptable quality signal is being recorded, LED #2 remains in a steady state. If a problem is encountered that cannot be resolved by the hardware or firmware (e.g., adjusting the active pressure on the sensor or resetting the SpO$_2$ measuring circuit), LED #2 is programmed to begin to blink rapidly until the physiological monitoring system is turned off. Alternatively, as a method to further conserve power, LED #2 could be activated only when a problem occurred, such as poor signal quality. LED #1 should be turned on only when no light is being measured by the photo diode, indicating the user has removed the physiological monitor from his or her forehead but has not turned the device off.

LED diodes were selected as functionality indicator due to their low power consumption and luminescence in a dark room. The selection of this component does not preclude the use of other types of visual (LCD) or audio stimuli for the functionality indicator.

I. Enclosure

The size of the enclosure 54 should be minimized so that the side of the enclosure does not rest on the user's pillow when he/she is sleeping on his/her side or stomach. To accommodate replacement of the battery inside the enclosure a removable cover can be utilized 58. When rechargeable batteries are utilized, the top and bottom of the enclosure is affixed with screws. Alternatively, when flat or coin-cell removable batteries are used, the top of the enclosure should include "L"-shaped sides approximately 0.7 cm long on both the length and width edges. When the enclosure cover is snapped into place, these edges will help form the sides of the enclosure. A small cutout in the PC board will allow both sides of the battery to be grasped for removal.

Compressed foam material ("stabilizing pad") is inserted into the physiological monitor, to apply a constant pressure to stabilize the sensor against the forehead 81. To direct the force from the stabilizing pad directly to the sensor, a channeling system, such as a plastic shielding 82 can be used.

J. Active Pressure SpO$_2$ Sensor

In one embodiment of the physiological monitoring system 12, foam is utilized to control the amount of pressure applied to the SpO$_2$ sensor against the forehead. When this approach is used, the foam should be replaced after each use since sweat can be absorbed during use. Also the resiliency of the foam deteriorates over time, resulting in variability in the amount of pressure applied. Since the use of passive (e.g., foam) methods for applying pressure on the SpO$_2$ sensor against the forehead can be imprecise, SpO$_2$ signal quality can be compromised. For example, the amount of pressure applied by the stabilizing pad 81 increases (decreases) when the enclosure pad 80 compresses too far (little) as a result of too much (or too little) tension applied by the elastic headband 83 (see FIG. 7). The headband is preferably adjustable for fit. Too much pressure, however, can result in poor blood profusion and a low amplitude AC component in the red and infrared signals. With too little pressure, the intensity of the reflected red and infrared light can be diffused. As an alternative to passive pressure, an active pressure system can be employed. Active pressure requires a system for monitoring the amount of pressure being applied to the SpO$_2$ sensor and a method for changing and/or maintaining the amount of pressure.

Figure 12:
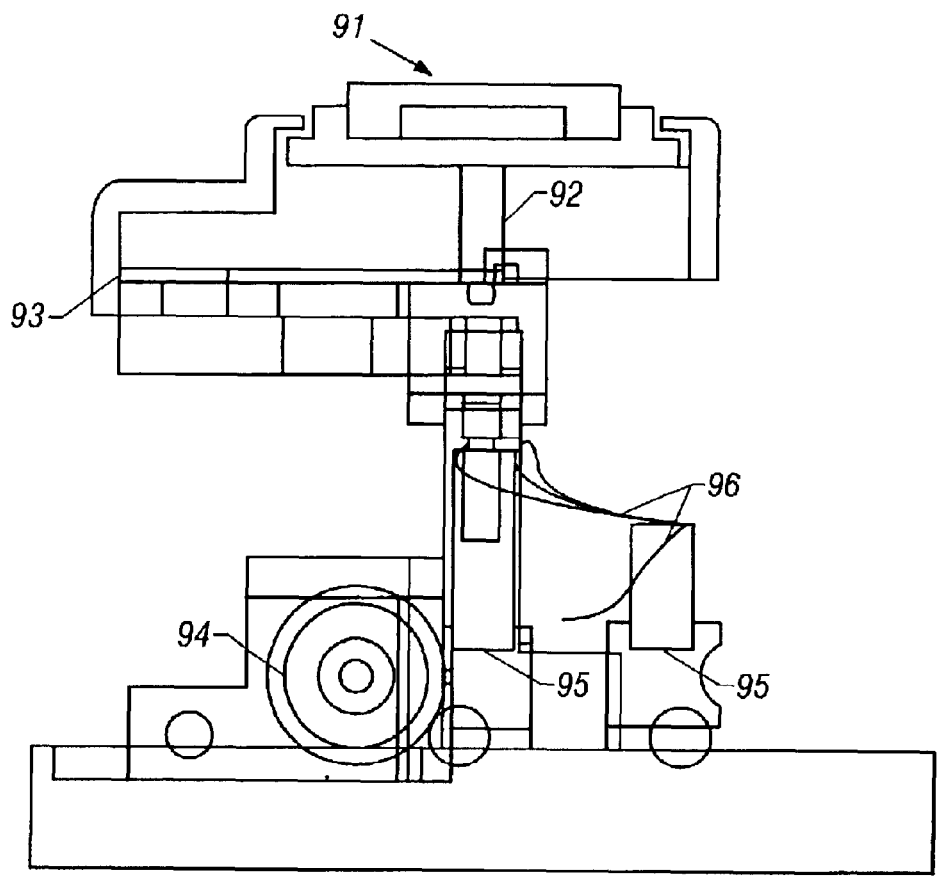
FIG. 12 illustrates an $SpO_2$ active pressure device.

FIG. 12 provides an illustration of an active pressure system for use in accordance with the present invention. The reflectance sensor 91 is attached to a post 92 that terminates as a tip that seats into a hole in a strain gauge 93. To accommodate between-subject differences in the curvature of the forehead, the shape of the tip allows the sensor pressure to be measured by the strain gauge, even when the sensor is not exactly perpendicular to the strain gauge. The amount of pressure that is applied to the sensor can be adjusted through the activation of a servo-motor 94, a worm gear 95, and a drive ramp 96. To increase pressure, the servomotor and worm gear cause the drive ramp to push the sensor toward the forehead. Using the strain gauge to monitor pressure, once the desired sensor pressure is achieved, the servomotor can be turned off and the worm gear deactivated so that the desired pressure is maintained without requiring any additional power.

When active pressure is utilized, the micro-controller can monitor both sensor pressure (via the strain gauge) and signal quality (based on the red and infrared signals). The pressure applied to the sensor can then be modified throughout the night as required to obtain high quality data recordings.

2. Method for Identifying Desaturations Associated with Respiratory Events

A. Measuring Oxyhemoglobin Saturation

The process of measuring oxyhemoglobin saturation in accordance with the present invention, after data has been collected, follows generally accepted principals. The red and infrared light 72 signals reflected from the tissue are detected by a photosensitive probe or light sensor 74, amplified and digitized by an A/D converter. Then, the direct-current (DC) and alternating current (AC) components of both signals are determined. From this data, the saturation ratio (r) is calculated as:

$$r = \frac{AC_{red}/DC_{red}}{AC_{infrared}/DC_{infrared}}$$

This saturation ratio determines the oxygen saturation by the formula:

$$S = ar + b$$

The constants a and b have approximate values a≈−25 and b≈110, respectively. The true values should be determined experimentally in the process of instrument calibration. This linear model gives good results if oxygen saturation is in the range from 90% to 100%. For smaller values of saturation the quadratic model may be used:

$$S = cr^2 + dr + e$$

where the constants o, d, and e are determined so that a best fit is obtained between experimental data and measurements performed by an accurate oximeter.

When the oxygen saturation is found, the oxygen partial pressure can be calculated using the well-known Hill's equation:

$$S = 100 \frac{(pO_2)^n}{(pO_2)^n + (p50)^n}$$

where n≈2.8 and $pO_2$ is the partial pressure of oxygen when S=50%. From the Hill's equation, the partial pressure of oxygen is finally found as $$pO_2 = p50 \left( \frac{S/100}{1 - S/100} \right)^{1/n}$$

B. SpO₂ Measuring Circuit

Measurement of $SpO_2$ requires an A/D converter with a wide dynamic range to accommodate variability in the AC and DC components. The AC component is approximately one hundred times smaller than the DC component. Approximately eight to ten bits of resolution is preferred for accurate representation of the AC component, with an additional six to seven bits of resolution for the DC component. To accommodate the significant between-subject differences in the DC component, an additional two to four bits of resolution is desired. One option to accommodate the requirements for a wide dynamic range is to use a high resolution A/D converter (20-bit or more), such as described in U.S. Pat. No. 5,820,550 to Polson et al. High resolution A/D converters, however, are generally limited by their longer conversion time and increased power consumption. Alternatively, one could use an analog circuit to separate the AC and DC components and one could use different amplifiers (see, for example, U.S. Pat. No. 4,407,290 to Wilber) or analog circuits to save the DC component between samples. The limitation of this approach is the inaccuracy of analog circuits due to variability of the active and passive components.

In the preferred embodiment in accordance with the invention, the largest part of the signal (the DC component) is subtracted through the use of a digitally set current generator and digitally adjusted gain to obtain a high resolution AC signal. The advantage of this approach is that expensive, slow, and power hungry A/D converters are not required, the length of stimulation of the red and infrared LED diodes and the associated power consumption is reduced, and high speed 12-bit successive approximation A/D converters commonly incorporated into microcontrollers can be utilized.

Figure 13:
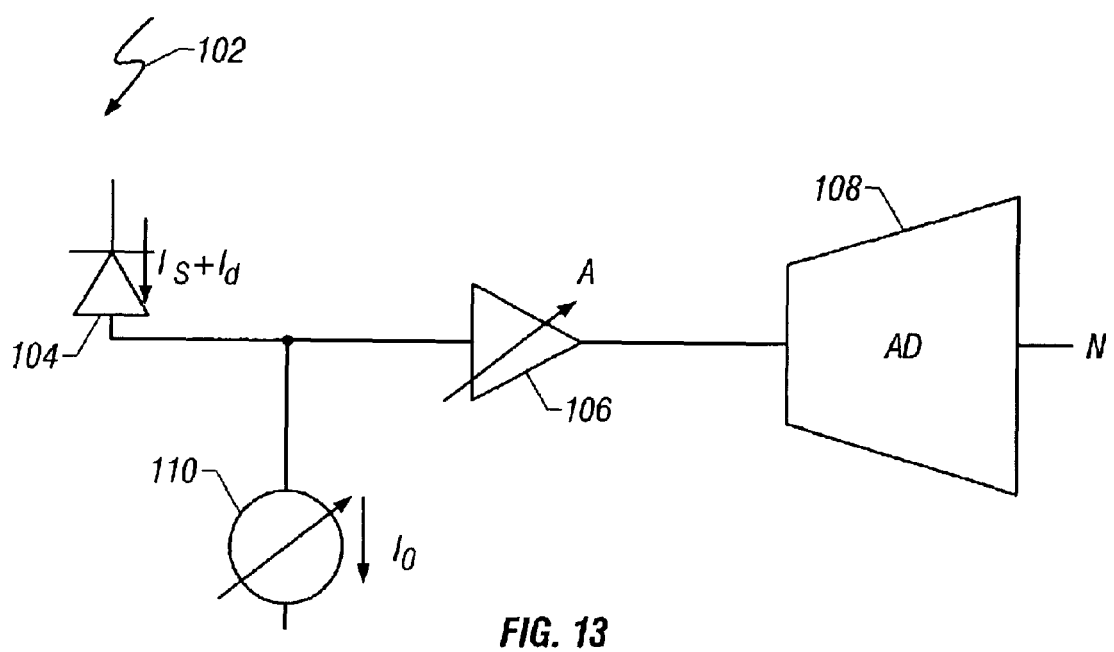
FIG. 13 is a block diagram of the $SpO_2$ measuring circuit for the system illustrated in FIG. 2.

The $SpO_2$ measurement circuit of FIG. 13 includes red (660 nm) and infrared (940 nm) light emitting diodes (LEDs) 102 with micro-controller controlled drivers, photo diode 104, appropriate amplifier 106 and A/D converter 108. Light from the LEDs is received at the photo diode. To provide the large dynamic range for the photo diode signal, two techniques are used. First, a digitally set current $I_0$ from a current source 110 is subtracted from the signal current $I_s + I_d$, thereby significantly reducing the DC component in the signal at the A/D converter Input. The AC and DC components of the resulting A/D input current are then in a similar range so that both components can now be accurately measured. Second, the gain (G) of the amplifier (A) is digitally set to ensure the AC component value at the A/D converter input is always within predefined limits (i.e., gain is increased more when the AC component is very small). The predefined limits can be experimentally determined, as will be known by those skilled in the art.

The amplifier (A) 106 is then used to amplify the difference between signal current from the photo diode 104 and the digitally-set constant current from the controlled source 110, and convert it to a voltage suitable for the A/D converter 108. This transformation shifts the available dynamic range to the required range. Additionally, the dynamic range can be changed by making the gain adjustment with a digitally-set potentiometer. A basic circuit diagram for the $SpO_2$ measuring circuit of the preferred embodiment is shown in FIG. 13.

The diode current consists of a component proportional to reflected light $I_s$ and "dark" current $I_d$ that depends on temperature and diode construction. From basic electrical laws, turning to FIG. 13, the values obtained after A/D conversion N are proportional to the relationship: $N \sim G*(I_s + I_d - I_0)$. The value needed for the reflected light inducing circuit is: $I_s \sim N/G + I_0 - I_d$, where G is amplifier transconductance [G]. During the adjustment phase, the values $I_0$ and G are set by digital potentiometers (multiplying D/A converters) so that the amplifier output signal is set within the A/D converter dynamic range with sufficient AC amplitude. Both values (G and $I_0$) can be adjusted during operation, when required.

For each sample that is acquired, three measurements are performed: one with the red LED on, one with the infrared LED on, and one with both LEDs off. The result of the third measurement is subtracted from the previous two, because it contains all offsets (amplifier and A/D converters) and ambient light influence. Taking into account that, for the $SpO_2$ calculation, a ratio of AC to DC component of light signal is required, the ratio for both light components, red and infrared, can be obtained. Min and max indexes correspond to values on minimum and maximum blood pressure, respectively, during heart activity period.

$$R_1 = AC/DC = (I_{smax} - I_{smin})/((I_{smax}+I_{smin})/2) = (N_{max}-N_{min})/((N_{max}+N_{min})/2+N_0)$$

The constant $N_0 = G^*(I_0 - I_d)$ can be determined by calculation using circuit component values or obtained by calibrating each device.

C. Smoothing of the Calculated $SpO_2$ Values

Figure 14:
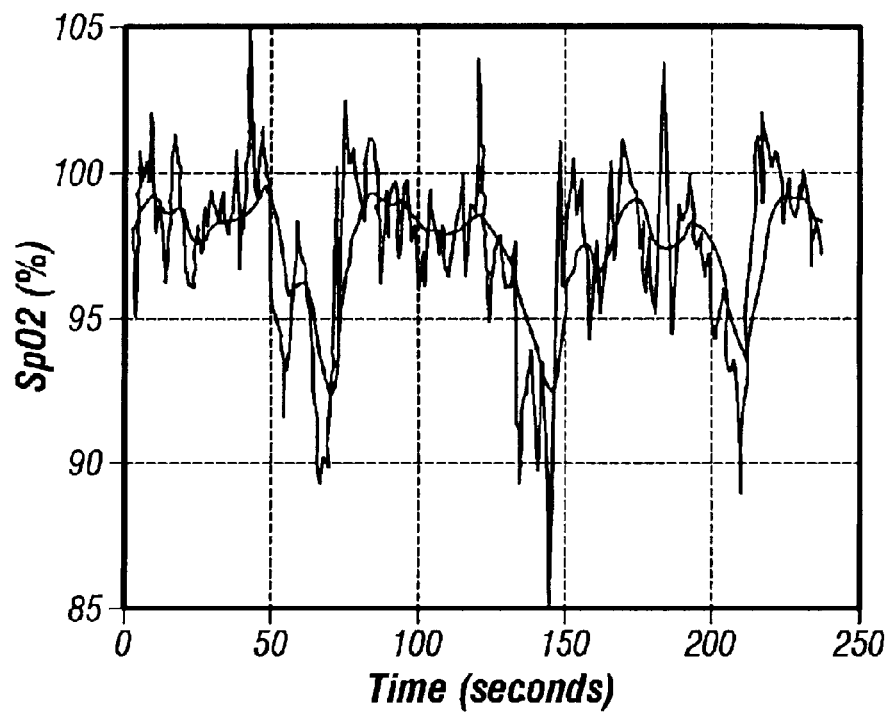
FIG. 14 illustrates the raw $SpO_2$ signal and after application of the three level smoothing algorithm.

The $SpO_2$ values calculated from red and infrared signals should be smoothed in order to reduce the effects of noise and increase the detection of desaturation events. In the preferred embodiment, this smoothing is done in three successive steps using median filtering, slew limitation, and averaging by IIR filtering. FIG. 14 displays a raw $SpO_2$ signal and the $SpO_2$ signal after application of the threestep smoothing. It should be understood that fewer than all three smoothing operations may be performed, and smoothed data produced from one smoothing operation may be used as data input for a next smoothing operation, in any sequence.

Step 1.

A 5-sample median filter is used in this application. The moving window consists of five consecutive samples. The samples are first ordered in non-decreasing order, and the central sample is taken as the median of the window. The current sample is replaced by the median value. The window is then moved to include the next sample, and the procedure is repeated.

Step 2.

In the preferred embodiment, a slew limitation operation is applied after the median filtering. Since the probability that two successive values of $SpO_2$ are dramatically different is very low, the possible rise or decrease of the $SpO_2$ can be limited by the slew limitation. For a simple slew adjustment, if the $SpO_2$ is rising, its rise is limited to +3% of the previous value, and if it is decreasing its decrease is limited to -3% of the previous value. In the preferred embodiment, the slew limitation incorporates the non-linear fit of the partial pressure curve. If the $SpO_2$ is rising, the rise is limited to 2%, 3%, 4% or 5% when the previous $SpO_2$ value is >97%, 94%, 89% or 80%, respectively. If the $SpO_2$ is falling, the fall is limited to 2%, 3%, 4% or 5% when the previous $SpO_2$ value is >97%, 94%, 89% or 80%, respectively. Finally, all values of $SpO_2$ are limited to be less than or equal to 100%.

Step 3.

In order to obtain better smoothing of the median-filtered and slew-limited $SpO_2$ signal, a first-order IIR filter is used. Its operation is described by the following equation:

$$SpO2\text{avg}[n] = k \times SpO2[n] + (1-k) \times SpO2\text{avg}[n-1]$$

where SpO2avg[n] denotes current smoothed sample, SpO2avg[n-1] denotes the previous smoothed sample, SpO2[n] denotes the current median-filtered and slew-limited $SpO_2$ sample, and k is a smoothing constant. In the preferred embodiment, k=0.20, however k in the range from 0.05 to 0.50 has been found to be acceptable.

D. Identifying Significant Desaturations

In order to identify abnormal respiratory events more accurately, a stepped approach to identify significant desaturations was empirically derived. This approach incorporates the fact that the oxyhemoglobin desaturation curve is non-linear. The model requires different levels of desaturation (measured from peak saturation to nadir) depending on the $SpO_2$ value at peak saturation to identify a significant saturation change.

Figure 15:
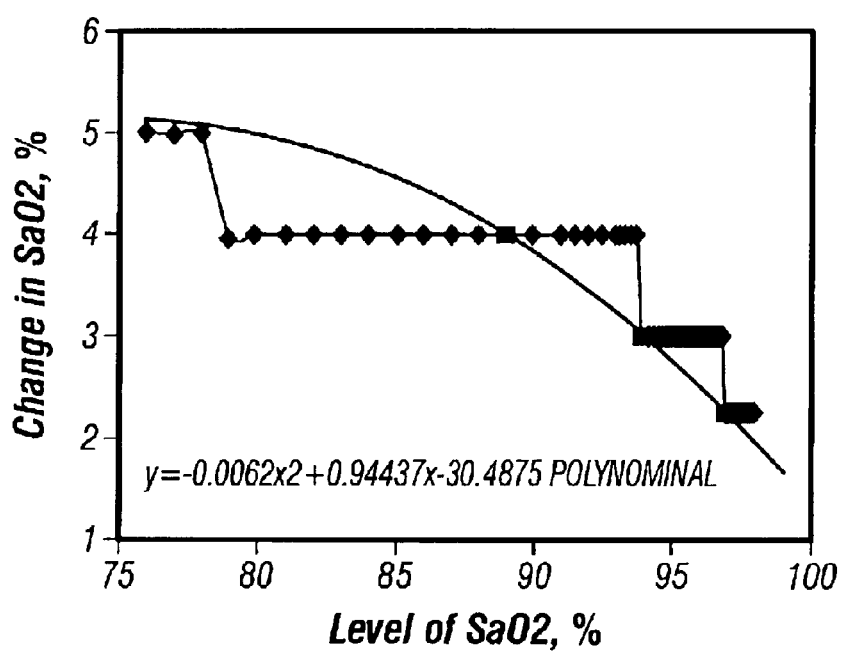
FIG. 15 illustrates the curve of the regression line for calculating required magnitude of desaturation based on the stepped approach.

To begin, a minimal threshold was empirically established requiring a 2.25% fall in $SpO_2$ for peak saturations >97%. Since the change in $pO_2$ from 98 to 97% is approximately 20 toor, the next step was established at 94%, or approximately a 20 toor $pO_2$ change from 97%. Additional steps were established at 89% and 80%, representing changes in toor of 14 and 11 respectively. A polynomial curve (see FIG. 15) was then fitted to the four steps: y=-0.0062x2+0.9437x-30.4875, where y is the required change in saturation and x is the peak saturation value.

In addition to identifying a minimum level of desaturation required for identification of abnormal respiratory events, the stepped approach is also applied to the resaturation. When the peak saturation is:

(1) >97%, a minimum of 2% resaturation from the nadir is required.

(2) <97% and >94%, a minimum 3% resaturation from the nadir is required.

(3) <94% and >89%, a 3.5% resaturation from the nadir is required.

(4) <89%, a 4% resaturation from the nadir is required.

Finally, each desaturation event (i.e., from the point of maximum saturation to the point of maximum resaturation) must be within the range from 5 to 60 seconds. As an alternative to using the polynomial equation to determine the required level of desaturation, the following criteria could be used to implement the stepped approach:

(1) >=97% at peak saturation, then >=2.25% change to nadir with at least a 2% recovery;

(2) <97% and >=94% at peak saturation, then >=3% change to nadir with at least a 3% recovery;

(3) <93% at peak saturation, then >=4% change to nadir with at least a 3.5% recovery.

Although these empirically derived values were selected for the preferred embodiment of the stepped approach based on the $pO_2$—$SaO_2$ relationship, alternative stepped approaches could be utilized so long as variable desaturation levels are applied.

E. Quantifying the Severity of the Desaturation

After meeting the rules described above, additional techniques were empirically derived in order to classify the desaturations into types. In the present preferred embodiment, a DE1 type is defined as a desaturation occurrence that has a high probability of being due to an obstructive sleep apnea or hypopnea. Although possible, a DE1 is rarely classified or indicated when the desaturation is less than 3%. A DE2 type is a desaturation that corresponds to a change in ventilation during sleep that may have clinical implications if a consistent pattern of DE2 type desaturations s is recognized. In the current preferred embodiment, DE1s were distinguished from DE2s based on two patterns. First, the slope of the DE 1 resaturation is quite steep. For example, a DE1 is classified when the nadir is >=86%, and at least a 3.8% recovery is detected in <=6 seconds from the nadir to the point of maximum resaturation. Alternatively, a DE1 is classified when at least a 4%, 5% or 6% recovery is detected in <=8, 10, or 12 seconds, respectively, from the nadir to the point of maximum resaturation. When the nadir is <86%, the recoveries are increased to 4.8%, 5%, 6%, and 7% for 6, 8, 10 and 12 seconds respectively. Second, the slope of the desaturation must decline steadily from the point of peak saturation. For example, if the peak saturation is:

>=98% and the $SpO_2$ decreases by 1.2% and then increases by 1%, or

<98% and >=93% and the $SpO_2$ decreases by 1.5% and then increases by 1.1%, or

<93% and >=88% and the $SpO_2$ decreases by 2.0% and then increases by 1.3%, or

<88% and the SpO$_2$ decreases by 2.5% and then increases by 1.7%, the peak saturation should be reestablished at the new maximum, and this process repeated recursively until the best peak saturation maximum is detected. Then the stepped approach is reapplied. If the stepped approach is not satisfied with the new peak saturation value, the event is a DE2. If the stepped approach is satisfied, the resaturation slope algorithms should be applied prior to classifying the event as a DE1. In addition to the rules described above, a DE2 can be changed to a DE1 if confirmed by the detection of an arousal as described below. The thresholds described above are influenced by the smoothing techniques applied to the SpO$_2$ signal. Therefore, alternative levels may be employed to identify the steady decrease and rapid increase in saturation associated with the recognition and classification of the desaturation. Thus, patient desaturation occurrences are classified into desaturation types according to the rate of change of SpO$_2$ desaturation and recovery, and the desaturation types may be utilized in clinical diagnosis of apnea risk. The number of desaturation types may be greater than two, and the multiple types may be used to quantify or classify the severity of desaturation for diagnostic purposes. Defining more than one desaturation type provides a method for improving the accuracy of classifying respiratory events, however, this classification step is not required.

F. Arousals Relating to Respiratory Events

The desaturations occurring with apneas or hypopneas due to obstruction of the upper airway are ended when the unsatisfied effort to breathe causes an arousal. The arousal allows return of pharyngeal dilator muscle activity sufficient to open the airway. An arousal is an abrupt change from a "deeper" stage of non-REM sleep to a "lighter" stage, or from REM sleep toward wakefulness, with the possibility of awakening as the final outcome. Arousal is often accompanied by increased tonic electromyographic activity and heart rate, as well as by body movement and a change in breathing pattern. A variety of definitions of transient EEG or cortical arousals have been proposed, most including a sudden speeding of the EEG, usually alpha rhythm, lasting two to 15 seconds. Desaturations not related to upper airway obstructions (i.e., a DE2 type desaturation, described above and further below) can be caused by decreased alveolar ventilation due to absent or decreased effort to breathe, in other words a central apnea or hypopnea. Central apneas and hypopneas may or may not be associated with transient arousals, but the arousals that do occur do so at the nadir of the desaturation, not preceding it as in obstructive events. Patient SpO$_2$ data signals that appear similar to desaturations can result from artifact attributed to gross head/body movements.

The capability to detect respiratory effort-related arousals would be useful as confirmation of desaturations due to abnormal respiratory events. Arousals can be readily detected with the physiological signals acquired in the preferred embodiment. For example, the heart rate, derived from the pulse rate measured by the pulse-oximeter, can increase rapidly (e.g., >10 beats per minute) in conjunction with an arousal. Proper quantification of the position sensor signal can detect changes in body position that can occur when the patient begins breathing again. During hypopneas, snoring levels increase in a crescendo pattern with each increased effort to breathe. When the patient awakens and starts breathing again, the sound level will suddenly change. During an apnea there is no airflow so there is no snoring. The breaths ending an apnea are commonly accompanied by a gasping or choking sound.

In an alternative embodiment of the invention (see FIG. 15), the measurement of airflow or nasal pressure can confirm that the desaturation is due to inspiratory flow limitation or a decrease in airflow as well as identify increases in airflow corresponding with arousals. Identification of faster-wave EEG signals could also be used to confirm an arousal if EEG is recorded.

In current practice, a clinician board-certified in sleep medicine is trained to visually recognize patterns across the various signals in order to differentiate obstructive-related respiratory events from the other types described above. Detection of the important changes in the signals can vary by clinician and only limited guidelines have been provided by professional organizations (e.g., American Academy of Sleep Medicine). The method utilized by the inventors to quantify the physiological signals in combination with automated pattern recognition is a novel application in the field of the invention.

As mentioned previously, to detect an arousal after a respiratory event, a minimum increase in heart rate of 10 beats per minute, for example, as compared to the average heart rate for a trailing windowing envelop can be used. In the preferred embodiment, the windowing envelope is a three-beat averaging window implemented with a two beat lag. By not including the two heartbeats immediately prior to heartbeat of interest, the transition to the rapid increase in the heart rate is avoided. In alternative embodiments, the averaging window can be decreased to one beat or increased to ten beats, and/or the lag period can range from zero to ten beats.

During PSG the position sensor is usually attached to the patient's trunk and is only used to identify the body position. When a position sensor is affixed to the head, however, it can be sensitive to subtle head movements associated with arousals from sleep. The inventors are unaware of any published reports in which a head position/movement sensor was utilized in this manner.

Gross head movements associated with body repositioning can be readily measured by the magnitude of change in amplitude of the signals (e.g., a change in amplitude between two data points exceeds 20% of the sensor's dynamic range). Subtle movements associated with arousals from sleep should be detectable by measuring variability in the signal, since the change in amplitude of the position sensor(s) during sleep is quite small. One method for identifying subtle arousals is to sum the absolute values of the amplitudes in successive data points within a detection window. When a sampling rate of 10 samples/second is utilized, subtle head/body position changes can be recognized when the summed change in amplitude in a one-second window exceeds 10% of the sensor's dynamic range. Alternatively, the detection of subtle movements that may be a result of an arousal can be detected using procedures similar to those described for detection of increased heart beats using a trailing windowing envelop. In another embodiment, thresholds are applied to the mean and coefficient of variation for a trailing window envelope to detect subtle movements. Since the dynamic range of the position sensor is dependant on the type used (i.e., accelerometer-, resistance- or capacitance-based), the thresholds should be empirically derived for the component selected. The key is that the position sensor is small and light so it can be mounted on the head, and sensitive to subtle changes in movement.

Methods for detecting patterns in human snoring sounds/level have previously been reported (see, for example, U.S. Pat. No. 6,045,514 to Raviv et al.). As mentioned previously, one of the unique features of the physiological monitoring system constructed in accordance with the present invention is that the microphone is optimally placed at a consistent distance (across individuals) with respect to the pharynx to measure snoring intensity. The snoring signal should first be transformed to convert the raw signal into a snoring level. In the preferred embodiment, an envelope detection transformation consisting of low pass filtering of the positive or negative values of a signal can be applied. Alternatively, the signal can be first be detrended to remove the linear and DC offsets, each data point converted to its absolute value, and the signal integrated over an empirically derived time window ranging from two to sixty seconds.

After the transformation is completed, the minimum and maximum snoring levels can be computed in order to establish the snoring intensity of the individual. Empirically derived thresholds can then be applied to detect changes in patterns of snoring sounds associated with crescendo snoring, gasps and choking sounds. Because snoring sounds occur primarily during inhalation, snoring is expected to follow a rhythmic pattern (i.e., the amount of time between snores should be relatively consistent for a given individual). The snoring interval can be computed by measuring the time lapse between increases in snoring levels. Crescendo snoring can be measured by comparing the magnitude of the snoring level to previous levels within the snoring pattern. An arousal from the hypopneac event occurs when the pattern of gradual increases in snoring levels is broken (i.e., a substantial reduction in snoring level). The cessation of the snoring pattern without a change in head position has a high probability if indicating an apneac event. An abrupt increase in snoring level terminating the cessation of sound indicates an arousal from an apneac event.

G. Classification of Respiratory Events

Results from the algorithms described previously that quantify the type of the desaturation and detect arousals can be combined to classify the type of respiratory event. The example provided in Table 1 demonstrates these results can be combined to more accurately identify significant obstructive respiratory events, as well as recognize other respiratory events that may have clinical implications.

TABLE 1

Use of Arousal Rules in the Classification of Respiratory Events

| Desaturation Rule | Arousal detected by | | | Obstructive Event | Obstructive/Central Event | Change in Alveolar Ventilation |
|---|---|---|---|---|---|---|
| | Heart Beat | Head Movement | Snoring | | | |
| DE1 | Yes | Yes | Yes | Yes | No | No |
| DE1 | Yes | No | No | Yes | No | No |
| DE1 | No | Yes | No | Yes | No | No |
| DE1 | No | No | Yes | Yes | No | No |
| DE1 | No | No | No | No | Yes | No |
| DE2 | No | No | No | No | No | Yes |
| DE2 | Yes | No | No | No | Yes | No |
| DE2 | No | Yes | No | No | Yes | No |
| DE2 | No | No | Yes | No | Yes | No |

3. ARES Questionnaire and ARES Profile Analysis

To improve the accuracy of the system 10, a method was developed for quantifying pre-existing risk factors for SA and assigning a prior probability of sleep apnea 18 that can be combined with the results from the physiological data into an integrated multi-variate classification model.

The analysis of pre-existing risk factors for SA includes, but is not limited to, responses to demographic, life-style and quality of life questions, including age, gender, body mass index (BMI), neck circumference, frequency and manifestation of excessive daytime sleepiness, frequency and magnitude of snoring, observed apneas, history of hypertension and use of alcohol. One hundred and twenty-eight questions were extracted from a clinical questionnaire applied in interviews with over 10,000 patients tested at major U.S. sleep laboratories.

Responses were obtained from 141 patients (99 males and 42 females, age 49.0+11.2 years) referred for overnight PSG and thirty healthy subjects (20 males and 10 females, age 37.8+12.3 years) recruited for sleep deprivation studies. The patient data included the respiratory disturbance index (RDI) obtained following full overnight PSG.

Subjects and patients were then assigned into four sleep apnea risk groups. The healthy subjects were classified as no risk based on extensive screening interviews and objective data collected during their participation in sleep deprivation studies. Patients with an RDI of 10 or less were classified as low risk. Patients with an RDI between 11 and 40 were grouped as moderate risk. Patients with an RDI greater than 40 were classified as high risk. The patient data were then submitted to linear correlation analysis to identify the variables that correlated with the RDI and risk group. A total of 11 predictive variables (plus gender) selected by this analysis were used in a discriminant function analysis (DFA) to predict the prior probability of risk for sleep apnea.

The results from the DFA ("ARES Profiler Analysis") are presented in Table 2 below. Results listed in each row correspond with the input classes (subjects and three patient groups). The number of subjects and patients classified by the DFA into each risk level is presented in the Distribution of Risk Level columns, followed by the percentage distribution into each risk level.

TABLE 2

Classification Results of the Preliminary ARES Profile Analysis

| Assignment Into Risk Groups | Classifications by the ARES DFA | | | | | | | | Total No. in each risk group |
|---|---|---|---|---|---|---|---|---|---|
| | Distribution by Risk Level | | | | Percentage by Risk Level | | | | |
| | No | Low | Mod. | High | No | Low | Mod. | High | |
| No Risk | 26 | 3 | 1 | 0 | 86.7 | 10.0 | 3.3 | 0.0 | 30 |
| Low Risk | 4 | 28 | 9 | 5 | 8.7 | 60.9 | 19.6 | 10.8 | 46 |
| Moderate Risk | 0 | 10 | 26 | 12 | 0.0 | 20.8 | 54.2 | 25.0 | 48 |
| High Risk | 1 | 4 | 10 | 32 | 2.1 | 8.5 | 21.3 | 68.1 | 47 |

The ARES Profile Analysis provided a sensitivity of 97.2% and a specificity of 90.0% with an overall classification accuracy of 94.7%. Since overnight PSG studies were not conducted on the healthy subjects, it is unclear whether the four misclassified "no risk" healthy subjects may in fact be at risk for SA (none were classified as high risk for sleep apnea). The four "low risk" patients classified by the DFA as "no risk" had RDI's of 0, 3, 5 and 7. Only one of the 95 patients with an RDI index corresponding with a moderate or high risk (i.e., RDI>10) for SA was classified as no risk. Since the RDI cut-offs selected to distinguish low, moderate and high risk for SA were arbitrary, some crossover of patients into the three "at risk" groups was to be expected. Yet, only 11% of the low risk patients were classified by the analysis as high risk for SA, and 8.5% of the high-risk patients were classified as having a low risk for SA.

4. Expert System Classification of Overall Risk for Sleep Apnea

As mentioned previously, the Apnea Risk Evaluation System (ARES) constructed in accordance with the present invention is an integrated system to assess the level of risk time with snoring void of respiratory events. An example of a portion of the logic used to assign overall risk for sleep apnea is presented in Table 3.

TABLE 3

Example of Expert Logic for Assigning Overall Risk Level

| ARES Overall Risk Level | Questionnaire Risk level | Epworth ≧10 | Overall ARDI | Positional | BMI >25 | Drinks Alcohol | High BP | Patient Comments |
|---|---|---|---|---|---|---|---|---|
| No | No | No | <5 | No | No | No | No | See physician for EDS (1) |
| Low | Low | Yes | <5 | No | No | No | No | Don't sleep on back (2) |
| Low | Low | No | <5 | Supine | No | No | No | Lose weight (3) |
| Low | Low | No | <5 | No | Yes | No | No | Don't drink alcohol at night (4) |
| Low | Low | No | <5 | No | No | Yes | No | 1, 2,, 3 and 4, monitor closely |
| Low-Moderate | Moderate | Yes | <5 | Supine | Yes | Yes | No | 1, 2, 3, and 4 PSG suggested |
| Low-Moderate | Moderate | Yes | <5 | Supine | Yes | No | Yes | PSG indicated |
| Moderate | High | Yes | <5 | No | Yes | No | Yes | See physician for EDS (1) |
| Severe | Low | Yes | >40 | No | Yes | No | No | Seek medical treatment |
| Severe | Moderate | Yes | >40 | No | Yes | No | Yes | Seek medical treatment |
| Severe | High | Yes | >40 | No | Yes | Yes | Yes | Seek medical treatment | for SA. Components of the system, including: (a) the physiological monitor that can be easily self-applied to the forehead and comfortably worn throughout the night to collect full-disclosure physiological recordings, (b) software which classifies types of respiratory events, and (c) a questionnaire and analysis (ARES Profile Analysis) which establishes an individual's prior probability of being at risk for SA, have been previously discussed. The expert system integrates outputs from these components in combination with a database of healthy subjects and patients in order to classify levels of risk for SA and generate a result report.

Results from the analysis of the data acquired from the physiological monitor will include computation of the: (a) total number of respiratory events (by and across types) across positions per hour of recording and over entire recording session and by position per hour of recording and over entire session; (b) average number of respiratory events (by and across types) per hour of recording time (RDI) across and by position over the entire session; and (c) number of 5-minute blocks of time with snoring void of respiratory events across and by position over the entire session. In addition, because daytime symptoms of sleep apnea (i.e., drowsiness and cognitive deficits) have proven more closely related to total time of nocturnal hypoxemia then to the RDI, this measure will also be calculated (e.g., percent time between 80% and 85%, and 85% and 90%.

Expert logic will then be applied to combine the summary results from the analysis of the physiological signals with the results from the ARES Profile Analysis. A look-up table will be developed to assign an overall risk level and present comments to assist with the interpretation of the risk level. In the preferred embodiment, the ARES RDI ("ARDI") will be based on time in bed, rather than time asleep (i.e., the physiological monitor will not include EEG necessary for recognizing sleep onset), the instructions will be to apply the device just prior to lights out. Rather than relying solely on the average RDI, as traditionally computed, the number and type of the respiratory events (e.g., obstructive, obstructive/ central, change in alveolar ventilation) may be included in the logic table, as well as the number of 5-minute blocks of A result report will be designed to meet the needs of both consumers and physicians. For consumers, the overall risk level and recommended actions could be provided. For physicians, the report could include a complete summary of the physiological signals and a full-disclosure presentation of the physiological recordings from the entire session.

5. Additional Signals May be Incorporated into the Physiological Monitor

Figure 16:
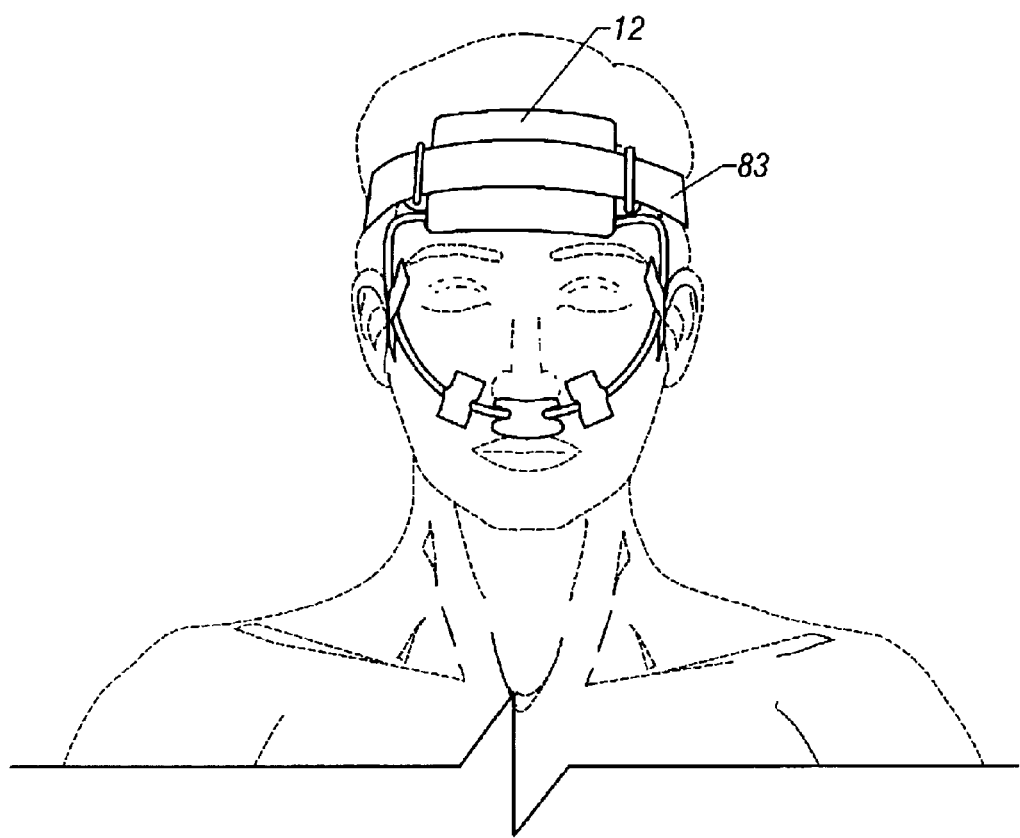
FIG. 16 shows the physiological monitor of FIG. 2 affixed on a patient's forehead in an alternative embodiment with an airflow sensor.

As discussed above, the PSG detects a number of signals. The present inventors, however, have found that not all signals are necessary to accurately detect sleep apnea. A reduction in the number of signals, as compared to PSG, is helpful in obtaining high quality data when the user is responsible for applying the device without assistance. Accordingly, the physiological monitor 12 in accordance with the preferred embodiment detects and records the pulse rate, oximetry, snoring sounds, and head position of a patient. In addition to these signals, the physiological monitor may also incorporate a number of additional signals without substantially increasing its weight, size, or power consumption. Note, however, that while additional signals may improve the accuracy of detecting respiratory events, these additional signals are not required. The inclusion of these additional signals could increase the complexity of system thereby affecting its ease of use. An airflow signal could be added to the physiological monitor with minimal intrusiveness. In this configuration, the amplifier and filtering circuitry for the airflow channel can be incorporated into the design with a connector provided in the enclosure for the termination of the sensor (see FIG. 16). A short wire or tube would then extend from the terminal connector to the sensor 100 positioned over the airway opening. The advantage of the forehead-mounted physiological monitor to acquire airflow would be to decrease the length of the connection between the sensor and recording device in order, thereby improving the reliability of the signal.

The physiological monitoring system could be readily adapted to acquire EEG, EOG or sub-mental EMG signals. These signals would assist in determining the user's sleep state and to detect arousals. Acquisition of high quality EEG could be readily obtained by the user without assistance, using systems such as described in U.S. Pat. No. 6,161,030. To acquire EEG or EMG signals, short wires could extend from the enclosure to the sensors. To acquire EOG, sensors centered at the left and right edge of the physiological monitor enclosure could provide positioning approximately above each eye. Disposable or reusable sensors could be inserted into a mechanism, which provides downward pressure against the skin when the physiological monitor is applied to the forehead. Application of these sensors in this manner would eliminate the need for the sensors to be taped in place by the user. Alternatively, short wires could extend from the enclosure to the sensors. Detection of fast or slow eye blinks, which would indicate the user is awake, may be utilized.

Although the physiological monitor 12 would become less comfortable to wear and more complex to apply, it could be modified to accept inputs from respiratory effort sensors. In this configuration, wires would connect the sensors around the chest and/or abdomen to the terminal connector (s) in the enclosure. Although attachment of the physiological monitoring device to the forehead is the preferred embodiment, the physiological monitoring device could be attached to the body in order to reduce the length of the wires from the respiratory effort sensors.

Acquisition of ECG signals would generally be redundant to the pulse rate signal derived from the red and infrared $SpO_2$ signals. Pulse transit time, as determined by the length of time between each heartbeat measured by the ECG and the pulse, however, might provide an improved measure of autonomic nervous system arousal. ECG signals of acceptable quality could be acquired with sensors placed over prominent bones located on each side of the heart (e.g., collar bones) with the wires extending from the enclosure to the sensors.

Figure 10:
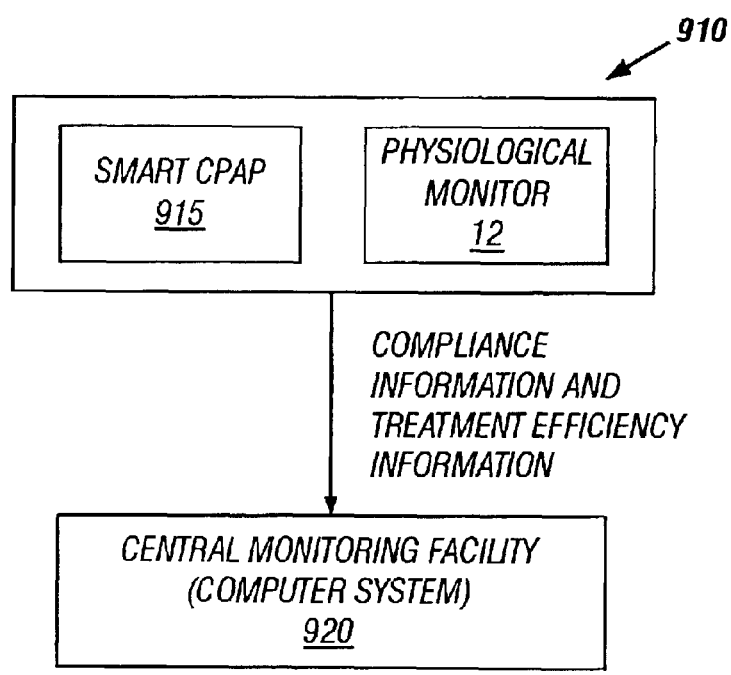
FIG. 10 is a block diagram of a CPAP incorporating the physiological monitor system of FIG. 2.

6. Integration of the Physiological Monitoring System with Other Therapeutic Devices FIG. 10 is a block diagram representation of the physiological monitor of the present invention integrated with a CPAP device. The integrated device 910 contains both a CPAP with the "smart system" (hereinafter referred to as "smart CPAP") (that monitors compliance by recording and storing the time the CPAP device is on at the prescribed pressure) and the physiological monitor 12 of the present invention. By incorporating the physiological monitor, the integrated device 910 not only monitors compliance, but also provides data on the efficacy and the time of use of the CPAP. When used routinely as part of the smart CPAP headgear (integrated device 910), the data analysis procedures of the current invention may be implemented in real-time so that only summary data (i.e., the occurrence and duration of respiratory events) would be stored for periodic review to assess the fit of the mask and adjustment of the pressure, rather than storing a full-disclosure recording. In the preferred embodiment, respiratory events would be monitored in real-time using a digital signal processing chip or micro-controller capable of processing the data (or signals).

To provide information to employers and clinicians, a system which contains the capability to download and transmit both the compliance information provided by the smart CPAP unit 915 and the treatment efficacy information provided by the physiological monitor 12 would be utilized. In the preferred embodiment, the system would include wireless or web-enabled transmission of data to a central monitoring facility capable of storing said data and making comparisons to historical data for that patient. The system would include feedback mechanism to notify designated parties when either compliance or treatment efficacy violates parameters established by the patient's physician, employer, home health care provider and/or by state or federal regulation. For example, if the patient is compliant with CPAP usage, but the number of respiratory events exceed a threshold established by the interested parties, the patient's home health care provider could be automatically notified to make an appointment to fit the patient with a new CPAP mask and/or adjust the CPAP pressure.

7. Physiological Monitoring System with Neuromuscular Stimulation

Using the physiological monitoring system constructed in accordance with the present invention, systems that stimulate muscles and nerves, for example, as discussed in patents '316, '655, and '216 reference above, maybe improved. In general, neuromuscular stimulation deals with controlling a tissue, muscle, or appropriate part of the body in a constructive matter to achieve a desired result. For example, patent '216 suggests a method for opening an upper airway by electrically stimulating a certain nerve. Similarly, patent '316 suggests a method of stimulating muscle and nerve tissue in a manner to help open blocked airways. Because the physiological monitor of the present invention, includes a $SpO_2$ sensor capable of detecting upper airway blockage, an embodiment that determines oxygen desaturation in real time could provide feedback to the neuromuscular stimulation device also in real time to adjust the magnitude and duration of stimulation, for example, in the embodiment as suggested by patent '216. Using the physiological monitor of the present invention, the stimulation of the appropriate nerve and or muscle may not necessarily be timed with respiration but be timed by other factor, such as the level of oxygen saturation detected and transmitted by the physiological monitor to the stimulation device.

Patent '316 discusses the use of microstimulators such as BION™ stimulator devices available from Advanced Bionics Corporation of Sylmar, Calif. One embodiment described in patent '316 requires a device to house the transmission coil supporting the sensing and telemetry functions. Information from the sensing function is transmitted from the sensing BION device to an external bedside controller, which utilizes such information to decide when and what stimulation is required to alleviate the occlusion. The bedside controller transmits stimulation commands to one or more of the BION implant devices.

Figure 11:
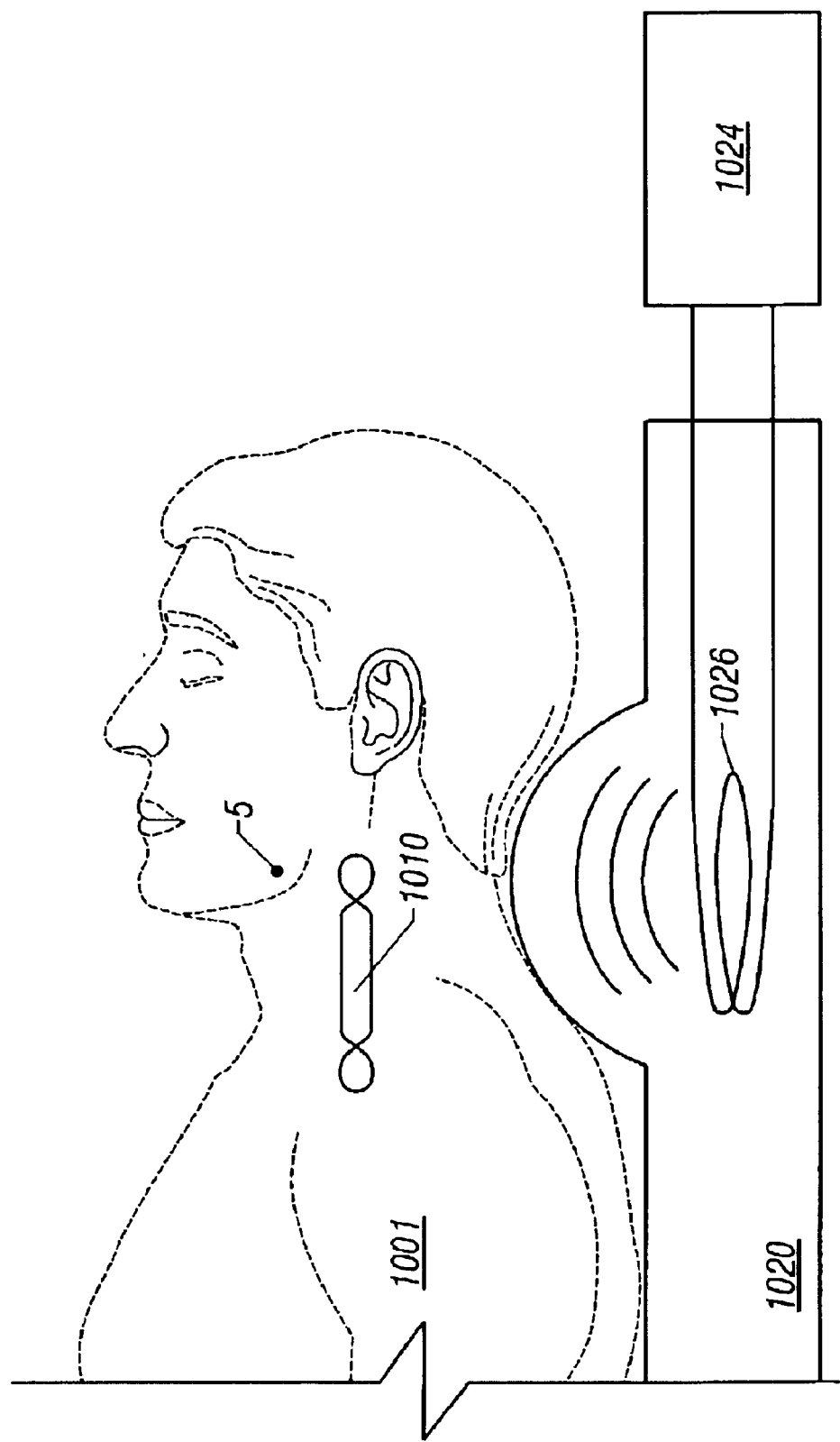
FIG. 11 illustrates one way in which microstimulators may be used to treat sleep apnea in accordance with the invention.

Referring to FIG. 11, one or more BION implant devices 1010 may receive power and command signals from a transmission coil 1026 placed under the patient 1001. An external bedside controller 1024 that is powered by conventional power lines sends a preprogrammed sequence of stimulation commands to the implant device(s) 1010, causing them to stimulate motor and/or sensory nerves at target sites 1005. The transmission coil may be located under the pillow or mattress 1020 or worn on the patient, and included as part of a collar around the neck, a vest, or other suitably located garment (not shown in FIG. 11).

The physiological monitor constructed in accordance with the present invention provides an appropriate alternative to house the transmission coil and controller described in patent '316. The micro-controller used to command the BION stimulators could be the same chip(s) used to control the pulse-oximetry. The transmission coil and the circuitry of the physiological monitor as shown in FIGS. 2–6 could use the same set of batteries. Combining these circuits would result in a lightweight easy to apply alternative, eliminating the need for a bedside controller as suggested in patent '316. Alternatively, coupling the BION technology with the current invention to monitor for respiratory events could eliminate the need to time the neuro-stimulation with respiration. This approach to treat sleep apnea was not considered in either patent '316 or patent '655.

The present invention has been described above in terms of a presently preferred embodiment so that an understanding of the present invention can be conveyed. There are, however, many configurations for a physiological monitor that is affixed on a patient's forehead not specifically described herein but with which the present invention is applicable. The present invention should therefore not be seen as limited to the particular embodiments described herein, but rather, it should be understood that the present invention has wide applicability with respect to monitoring and collecting physiological data. All modifications, variations, or equivalent arrangements and implementations that are within the scope of the attached claims should therefore be considered within the scope of the invention.

We claim:

1. A system that monitors respiratory events of a patient, the system comprising:
   a physiological monitoring system;
   means for removably affixing the physiological monitoring system to the patient's forehead;
   a pulse oximetry sensor and circuitry that detects oxyhemoglobin saturation and pulse rate of the patient of the patient and produces corresponding pulse oximetry data signals;
   a storage memory for storing the pulse oximetry data signals produced by said pulse oximetry sensor;
   wherein said pulse oximetry sensor and said storage memory are mounted on the physiological monitoring system, eliminating all lead wires between the patient and the storage memory, and such that the pulse oximetry sensor detects said oxyhemoglobin saturation and pulse rate of the patient and produces said pulse oximetry data signals, thereby monitoring the patient's condition; and
   computing circuitry that receives said pulse oximetry data signals and identifies a respiratory event of the patient responsive to said pulse oximetry data signals, wherein the computing circuitry identifies said respiratory event in response to detecting pulse oximetry data signals that indicate a variable threshold level of oxyhemoglobin desaturation, and wherein the variable threshold level is based on at least one of the following criteria: peak oxyhemoglobin saturation, nadir, and peak oxyhemolobin resaturation.

2. A system as defined in claim 1, wherein the system monitors sleep related obstructive respiratory events of a patient during sleep.

3. A system as defined in claim 1, further comprising a patient head position and movement sensor that produces a head position and movement signal that indicates position and movement of the patient's head.

4. A system as defined in claim 1, further comprising means for producing a sound data signal that indicates detected sounds produced by said patient.

5. A system as defined in claim 1, wherein said means for removably affixing the physiological monitoring system to the patient's forehead comprises an adjustable strap.

6. A system as defined in claim 1, further comprising a computing device that receives said pulse oximetry data signals and computes $SpO_2$ measurement from which a respiratory event may be identified.

7. A system as defined in claim 1, further comprising a data transfer interface that communicates the pulse oximetry data signals from the system to an external computing device.

8. A system as defined in claim 1, wherein said pulse oximetry sensor is a reflectance-type sensor.

9. A system as defined in claim 1, wherein the pulse oximetry sensor comprises an active pulse oximetry sensor that applies positive pressure on the patient.

10. A system as defined in claim 1, further comprising a patient respiratory airflow detector.

11. A system as defined in claim 10, wherein the airflow detector comprises a nasal cannula or a pressure transducer.

12. A system as defined in claim 1, further including:
    a data transfer interface that communicates said pulse oximetry data signals to the computing circuitry;
    wherein the computing circuitry analyzes the pulse oximetry data signals and computes time spent by the patient at each of a plurality of oxyhemoglobin saturation levels.

13. A system as defined in claim 1, further comprising a CPAP device, and wherein said system monitors effects of the CPAP device.

14. A system as defined in claim 1, whereby the threshold level of oxyhemoglobin desaturation is variable.

15. A system as defined in claim 1, wherein values of the pulse oximetry data signal that indicate the threshold level of oxyhemoglobin desaturation are variable.

16. A method of evaluating risk of sleep apnea in a patient, the method comprising:
    attaching a physiological monitoring system to a patient's forehead, wherein the physiological monitoring system includes (a) a pulse oximetry sensor and circuitry that detects oxyhemoalobin saturation and pulse rate of the patient and produces corresponding pulse oximetry data signals, and (b) a storage memory that stores the pulse oximetry data signals produced by said pulse oximetry sensor, thereby eliminating all lead wires between the patient and the storage memory;
    providing the stored pulse oximetry data signals to an expert system that receives the stored pulse oximetry data signals, wherein the expert system performs an analysis and generates a sleep apnea risk evaluation report of the patient;
    receiving light from multiple light sources of an $SpO_2$ measuring circuit at a photo diode that produces a photo diode current; and
    producing a difference signal at an input of an analog-to-digital converter, wherein the difference signal comprises the difference between the photo diode current and a substantially constant current produced by a controlled current source, the difference input signal having an AC component and a DC component, the analog-to-digital converter producing a measurement current in response to the difference input signal, wherein the substantially constant current is selected such that the difference input signal AC component is substantially equal to the DC component.

17. A system that monitors respiratory events of a patient, the system comprising:
    a physiological monitoring system;
    means for removably affixing the physiological monitoring system to the patient's forehead;
    a pulse oximetry sensor and circuitry that detects oxyhemoglobin saturation and pulse rate of the patient of the patient and produces corresponding pulse oximetry data signals;
    a storage memory for storing the pulse oximetry data signals produced by said pulse oximetry sensor; and computing circuitry that receives said pulse oximetry data signals and identifies a respiratory event of the patient responsive to said pulse oximetry data signals, wherein the computing circuitry identifies said respiratory event in response to detecting pulse oximetry data signals that indicate a threshold level of oxyhemoglobin desaturation;

wherein said pulse oximetry sensor and said storage memory are mounted on the physiological monitoring system, eliminating all lead wires between the patient and the storage memory, and such that the pulse oximetry sensor detects said oxyhemoglobin saturation and pulse rate of the patient and produces said pulse oximetry data signals, thereby monitoring the patient's condition, wherein the threshold level of oxyhemoglobin desaturation is variable, and wherein the variable threshold level is based on a known relationship between the partial pressure of oxygen and oxyhemoglobin saturation.

18. A system that monitors respiratory events of a patient, the system comprising:

a physiological monitoring system;

means for removably affixing the physiological monitoring system to the patient's forehead; and a pulse oximetry sensor and circuitry that detects oxyhemoglobin saturation and pulse rate of the patient of the patient and produces corresponding pulse oximetry data signals;

a storage memory for storing the pulse oximetry data signals produced by said pulse oximetry sensor;

wherein said pulse oximetry sensor and said storage memory are mounted on the physiological monitoring system, eliminating all lead wires between the patient and the storage memory, and such that the pulse oximetry sensor detects said oxyhemoglobin saturation and pulse rate of the patient and produces said pulse oximetry data signals, thereby monitoring the patient's condition, and wherein said physiological monitoring system interfaces with and provides feedback to a neuromuscular stimulation device and that monitors efficacy of the neuromuscular stimulation device.

19. A risk evaluation system that monitors sleep-related obstructive respiratory events of a patient and provides a patient risk evaluation, the system comprising:

(a) a physiological monitoring system that includes (i) a pulse oximetry sensor and circuitry that detects oxyhemoglobin saturation and pulse rate of the patient and produces corresponding pulse oximetry data signals, thereby monitoring said patient's condition, (ii) a storage memory that stores the pulse oximetry data signals produced by said pulse oximetry sensor, and (iii) means for removably affixing the physiological monitoring system to the patient's forehead, whereby all lead wires between the patient and the storage means are eliminated;

(b) an expert system;

(c) a data transfer interface that communicates said pulse oximetry data signals to the expert system;

wherein the expert system receives and analyzes the pulse oximetry data signals and generates a sleep apnea risk evaluation report of the patient; and (d) a computing system that receives and analyzes the pulse oximetry data signals and identifies any abnormal respiratory events of the patient, thereby producing at least one secondary respiratory event signal that is provided to the expert system.

20. A system that monitors respiratory events of a patient, the system comprising:

a physiological monitoring system;

means for removably affixing the physiological monitoring system to the patient's forehead;

a pulse oximetry sensor and circuitry that detects oxyhemoglobin saturation and pulse rate of the patient of the patient and produces corresponding pulse oximetry data signals;

a storage memory for storing the pulse oximetry data signals produced by said pulse oximetry sensor;

wherein said pulse oximetry sensor and said storage memory are mounted on the physiological monitoring system, eliminating all lead wires between the patient and the storage memory, and such that the pulse oximetry sensor detects said oxyhemoglobin saturation and pulse rate of the patient and produces said pulse oximetry data signals, thereby monitoring the patient's condition;

a patient head position and movement sensor that produces a head position and movement signal that indicates position and movement of the patient's head;

means for producing a sound data signal that indicates detected sounds produced by said patient;

a computing system;

a data transfer interface that communicates patient physiological data signals to the computing system, said patient physiological data signals including said pulse oximetry data signals, said head position and movement signal, and said sound data signal;

wherein the computing system analyzes the patient physiological data signals and identifies any abnormal respiratory events of the patient, classifying the analyzed data signals into one or more types of respiratory events; and an expert system that analyzes one or more patient physiological signals and detects patient arousals that can be used to confirm the respiratory event type classification.

21. A system as defined in claim 20, wherein said expert system summarizes any identified patient respiratory events and generates a patient report.

22. A system as defined in claim 20, wherein the expert system receives patient client clinical information, receives said patient physiological signals, and utilizes said patient clinical information and said patient physiological signals to confirm the respiratory event type classification.

23. A system as defined in claim 20, wherein said expert system receives patient clinical information, receives said patient physiological data signals, analyzes the physiological data signals and patient clinical information against a database of sleep apnea risk data, and generates a sleep apnea risk evaluation report of the patient.

24. A method of evaluating risk of sleep apnea in a patient, comprising the steps of:

measuring a patient's oxyhemoglobin desaturation; and comparing the patient's oxyhemoglobin desaturation with a threshold level of oxyhemoglobin desaturation required to determine a respiratory event, wherein the threshold level of oxyhemoglobin desaturation is variable, and wherein the variable threshold level is based on a known relationship between partial pressure of oxygen and oxyhemoglobin saturation.

25. The method of claim 24, wherein the variable threshold level is based on at least one of the following criteria:

peak oxyhemoglobin saturation, nadir, and peak oxyhemoglobin resaturation.

26. The method of claim 24, wherein the variable threshold level of oxyhemoglobin oxyhemoglobin desaturation is based at least in part on an automated detection of changes in patient snoring sounds, head movement, and pulse rate.

27. A physiological monitoring system comprising:
a pulse oximetry sensor and circuitry that detects oxyhemoglobin saturation and pulse rate of a patient and produces corresponding pulse oximetry data signals;
a power source that provides electrical energy to the sensor and circuitry for operation; and
a storage memory that stores the pulse oximetry data signals produced by said pulse oximetry sensor;
means for removably affixing said pulse oximetry sensor and circuitry, said power source, and said storage memory to the patient's forehead, and wherein said pulse oximetry sensor and circuitry, said power source, and said storage memory are affixed on said patient's body to detect the oxyhemolobin saturation and pulse rate and produce the corresponding data signals, provide electrical power, and store the data signals, respectively, thereby monitoring said patient's condition, and whereby all lead wires between the patient and the storage memory are eliminated; and
an $SpO_2$ measuring circuit comprising multiple light sources, a photo diode that receives light from the light sources and produces a photo diode current, a controlled current source that produces a substantially constant current, and an analog-to-digital converter that receives a difference input signal comprising the difference between the photo diode current and the constant current, the difference input signal having an AC component and a DC component, the analog-to-digital converter producing a measurement current in response to said difference input signal, wherein the substantially constant current is selected such that the difference input signal AC component is substantially equal to the DC component.

28. A risk evaluation system that monitors sleep-related obstructive respiratory events of a patient and provides a patient risk evaluation, the system comprising:
(a) a physiological monitoring system that includes (i) a pulse oximetry sensor and circuitry that detects oxyhemoglobin saturation and pulse rate of the patient and produces corresponding pulse oximetry data signals, thereby monitoring said patient's condition, (ii) a storage memory that stores the pulse oximetry data signals produced by said pulse oximetry sensor, and (iii) means for removably affixing the physiological monitoring system to the patient's forehead, whereby all lead wires between the patient and the storage means are eliminated;
(b) an expert system; and
(c) a data transfer interface that communicates said pulse oximetry data signals to the expert system;
wherein the expert system receives and analyzes the pulse oximetry data signals and generates a sleep apnea risk evaluation report of the patient, wherein the expert system receives patient clinical information, and wherein the expert system analyzes the patient clinical information and compares the patient clinical information to a database such that the patient is assigned into one of a plurality of discrete risk categories for sleep apnea.

29. A system as defined in claim 28, further including: a microphone that produces a sound data signal that indicates detected sounds produced by said patient.

30. A system as defined in claim 28, further including:
a patient head position and movement sensor that detects position and movement of the head of said patient and produces corresponding head position and movement data signals.

31. A system as defined in claim 28, further comprising computing circuitry that receives said pulse oximetry data signals and identifies a respiratory event of the patient, wherein the computing circuitry identifies said respiratory event in response to detecting pulse oximetry data signals that indicate a threshold level of oxyhemoglobin desaturation.

32. A system as defined in claim 31, wherein values of the pulse oximetry data signals that indicate oxyhemoglobin desaturation are variable.

33. A system as defined in claim 31, wherein the threshold level of oxyhemoglobin desaturation is variable.

34. A system as defined in claim 31, wherein the threshold level of oxyhemoglobin desaturation is variable, and wherein the variable threshold level is based on a known relationship between the partial pressure of oxygen and oxyhemoglobin saturation.

35. A system as defined in claim 31, wherein the threshold level of oxyhemoglobin desaturation is variable, and the variable threshold level is based on at least one of the following criteria: peak oxyhemoglobin saturation, nadir, and peak oxyhemoglobin resaturation.

36. A physiological monitoring system comprising:
a pulse oximetry sensor and circuitry that detects oxyhemoglobin saturation and pulse rate of a patient and produces corresponding pulse oximetry data signals;
a power source that provides electrical energy to the sensor and circuitry for operation; and
a storage memory that stores the pulse oximetry data signals produced by said pulse oximetry sensor;
means for removably affixing said pulse oximetry sensor and circuitry, said power source, and said storage memory to the patient's forehead, and wherein said pulse oximetry sensor and circuitry, said power source, and said storage memory are affixed on said patient's body to detect the oxyhemoglobin saturation and pulse rate and produce the corresponding data signals, provide electrical power, and store the data signals, respectively, thereby monitoring said patient's condition, and whereby all lead wires between the patient and the storage memory are eliminated; and
a computing device that receives patient $SpO_2$ data produced by the pulse oximetry sensor and identifies $SpO_2$ data that indicates desaturation related to abnormal respiratory events by identifying changes in patient physiological data that indicate patient arousal.

37. A system as defined in claim 36, further including:
a patient head position and movement sensor that produces a head position and movement data signal that indicates position and movement of the patient's head.

38. A system as defined in claim 36, further including: a microphone that produces a sound data signal that indicates detected sounds produced by said patient.

39. A system as defined in claim 36, further comprising a data transfer interface that communicates data from the system to an external computer.

40. A system as defined in claim 36, wherein the means for removably affixing the physiological monitoring system to the patient's forehead comprises an adjustable strap.

41. A system as defined in claim 36, wherein the computing device smooths the $SpO_2$ data by performing at least one of the following smoothing operations: (a) applying a moving window median filter that replaces a current data sample value with a median value selected from a predetermined number of data sample values, (b) applying a slew limitation filter that determines if two consecutive data sample values differ by more than a predetermined amount, and in response replaces a data sample value with a replacement value so as to limit the difference to no greater than the predetermined amount, and (c) applying an averaging technique that operates on multiple data sample values.

42. A system as defined in claim 41, wherein the averaging technique comprises a first-order infinite impulse response (IIR) filter that operates on a current data sample value and a previous data sample value.

43. A system as defined in claim 41, wherein the computing device performs multiple smoothing operations and one or more of the smoothing operations receives, as data input, smoothed data sample values produced by a different smoothing operation.

44. A system as defined in claim 36, wherein the computing device indicates desaturation occurrences in accordance with rate of change of $SpO_2$ desaturation data.

45. A system as defined in claim 36, wherein the pulse oximetry sensor comprises an active pulse oximetry sensor that applies positive pressure on the patient.

46. A system as defined in claim 36, wherein the changes in patient physiological data include at least one of changes in patient heart rate, patient position and movement, and patient produced sounds.

47. A system for monitoring respiratory events of a patient, the system comprising:
a physiological monitoring system including a pulse oximetry sensor and circuitry, and storage means for storing physiological data, the pulse oximetry sensor and circuitry detecting oxyhemoglobin saturation and pulse rate of a patient and producing corresponding pulse oximetry data signals, and the storage means storing a recording of the pulse oximetry signals; and
means for removably affixing said physiological monitoring system to the patient's forehead, whereby all lead wires between the patient and the means for storing are eliminated, the means for removably affixing comprising an elastic strap and at least one foam pad mounted to said physiological monitoring system, said elastic strap and foam pad cooperating to apply a pressure of the pulse oximetry sensor against the patient's forehead.

48. The system of claim 47, further comprising:
a power source that provides electrical energy to the pulse oximetry sensor and circuitry for operation; and
said means for storing comprises a storage memory that stores the pulse oximetry data signals produced by said pulse oximetry sensor;
wherein said power source and said storage memory are mounted on the physiological monitoring system.

49. The system of claim 47, wherein said pressure is optimized by adjusting the elastic strap and adjusting the thickness of said at least one foam pad.

50. The system of claim 49, further comprising means for measuring said pressure.

51. The system of claim 50, further comprising means for actively pressing the pulse oximetry sensor toward the patient's forehead.

52. A method of evaluating risk of sleep apnea in a patient, the method comprising:
attaching a physiological monitoring system to a patient's forehead, wherein the physiological monitoring system includes (a) a pulse oximetry sensor and circuitry that detects oxyhemoglobin saturation and pulse rate of the patient and produces corresponding pulse oximetry data signals, and (b) a storage memory that stores the pulse oximetry data signals produced by said pulse oximetry sensor, thereby eliminating all lead wires between the patient and the storage memory;
providing the stored pulse oximetry data signals to an expert system that receives the stored pulse oximetry data signals, wherein the expert system performs an analysis and generates a sleep apnea risk evaluation report of the patient; and
analyzing the pulse oximetry data signals and identifying any abnormal respiratory events of the patient, thereby producing one or more secondary respiratory event signals; and providing the secondary respiratory event signals to the expert system for analysis in generating the evaluation report.

53. A method as defined in claim 52, wherein the physiological monitoring system further includes a patient head position sensor that detects the position of the patient's head and produces corresponding head position data signals, and a microphone that detects snoring sounds produced by said patient and produces corresponding sound data signals, such that the physiological monitoring system thereby monitors said patient's condition.

54. A method as defined in claim 52, further including the expert system receiving the pulse oximetry data signals and utilizing a database to perform an analysis and generate the evaluation report of the patient.

55. A method as defined in claim 54, wherein the expert system receives patient clinical information and the expert system analyzes the patient clinical information using discriminant function analysis developed using information from a database.

56. A method as defined in claim 54, further comprising providing said pulse oximetry data signals to computing circuitry that responds to the received pulse oximetry data signals by identifying a respiratory event of the patient, wherein the computing circuitry identifies said respiratory event in response to detecting pulse oximetry data signals that indicate a threshold level of oxyhemoglobin desaturation.

57. A method as defined in claim 56, wherein values of the pulse oximetry data signals that indicate the threshold level of oxyhemoglobin desaturation are variable.

58. A method as defined in claim 56, wherein the threshold level of oxyhemoglobin desaturation is variable.

59. A method as defined in claim 52, further including receiving patient $SpO_2$ data produced by the pulse oximetry sensor and identifying $SpO_2$ data that indicates desaturation occurrences in accordance with rate of change of $SpO_2$ desaturation data.

60. A method as defined in claim 52, wherein the pulse oximetry sensor comprises an active pulse oximetry sensor that applies positive pressure on the patient.

61. A method as defined in claim 52, wherein the step of attaching the physiological monitoring system to the patient's forehead comprises affixing the physiological monitoring system to the patient's forehead by an adjustable strap.

62. A method as defined in claim 52, further comprising: receiving patient $SpO_2$ data produced by the pulse oximetry sensor; and smoothing the $SpO_2$ data by performing at least one of the following smoothing operations: (a) applying a moving window median filter that replaces a current data sample value with a median value selected from a predetermined number of data sample values, (b) applying a slew limitation filter that determines if two consecutive data sample values differ by more than a predetermined amount, and in response replaces a data sample value with a replacement value so as to limit the difference to no greater than the predetermined amount, and (c) applying an averaging technique that operates on multiple data sample values.

63. A method as defined in claim 62, wherein the averaging technique comprises a first-order infinite impulse response (IIR) filter that operates on a current data sample value and a previous data sample value.

64. A method as defined in claim 62, wherein more than one of the multiple smoothing operations is performed, and at least one of the smoothing operations receives, as data input, smoothed data sample values produced by a different smoothing operation.

65. A method of evaluating risk of sleep apnea in a patient, the method comprising:

attaching a physiological monitoring system to a patient's forehead, wherein the physiological monitoring system includes (a) a pulse oximetry sensor and circuitry that detects oxyhemoglobin saturation and pulse rate of the patient and produces corresponding pulse oximetry data signals, and (b) a storage memory that stores the pulse oximetry data signals produced by said pulse oximetry sensor, thereby eliminating all lead wires between the patient and the storage memory; and providing the stored pulse oximetry data signals to an expert system that receives the stored pulse oximetry data signals, wherein the expert system performs an analysis and generates a sleep apnea risk evaluation report of the patient, the expert system receiving the pulse oximetry data signals and utilizing a database to perform an analysis and generate the evaluation report of the patient;

wherein attaching the physiological monitoring system comprises attaching a system that further includes a patient head position and movement sensor that detects position and movement of the head of said patient and produces corresponding head position and movement data signals, and a microphone that produces a sound data signal that indicates detected sounds produced by said patient, wherein said pulse oximetry data signals, said head position and movement data signals, and said sound data signal comprise patient physiological data signals.

66. A method as defined in claim 65, further including receiving patient SpO$_2$ data produced by the pulse oximetry sensor and identifying SpO$_2$ data that indicates desaturation related to abnormal respiratory events by identifying changes in patient physiological data that indicate patient arousal.

67. A method as defined in claim 66, wherein the changes in patient physiological data include at least one of changes in patient heart rate, patient position and movement, and patient produced sounds.

68. A method as defined in claim 65, further including providing the patient physiological data signals to a computing system that analyzes the patient physiological data signals and identifies any abnormal respiratory events of the patient, thereby producing one or more secondary respiratory event signals that are provided to the expert system.

69. A method of evaluating risk of sleep apnea in a patient, the method comprising:

attaching a physiological monitoring system to a patient's forehead, wherein the physiological monitoring system includes (a) a pulse oximetry sensor and circuitry that detects oxyhemoglobin saturation and pulse rate of the patient and produces corresponding pulse oximetry data signals, and (b) a storage memory that stores the pulse oximetry data signals produced by said pulse oximetry sensor, thereby eliminating all lead wires between the patient and the storage memory;

providing the stored pulse oximetry data signals to an expert system that receives the stored pulse oximetry data signals, wherein the expert system performs an analysis and generates a sleep apnea risk evaluation report of the patient, the expert system receiving the pulse oximetry data signals and utilizing a database to perform an analysis and generate the evaluation report of the patient; and providing said pulse oximetry data signals to computing circuitry that responds to the received pulse oximetry data signals by identifying a respiratory event of the patient, wherein the computing circuitry identifies said respiratory event in response to detecting pulse oximetry data signals that indicate a threshold level of oxyhemoglobin desaturation;

wherein the threshold level of oxyhemoglobin desaturation is variable, and wherein the variable threshold level is based on a known relationship between the partial pressure of oxygen and oxyhemoglobin saturation.

70. A method of evaluating risk of sleep apnea in a patient, the method comprising:

attaching a physiological monitoring system to a patient's forehead, wherein the physiological monitoring system includes (a) a pulse oximetry sensor and circuitry that detects oxyhemoglobin saturation and pulse rate of the patient and produces corresponding pulse oximetry data signals, and (b) a storage memory that stores the pulse oximetry data signals produced by said pulse oximetry sensor, thereby eliminating all lead wires between the patient and the storage memory;

providing the stored pulse oximetry data signals to an expert system that receives the stored pulse oximetry data signals, wherein the expert system performs an analysis and generates a sleep apnea risk evaluation report of the patient, the expert system receiving the pulse oximetry data signals and utilizing a database to perform an analysis and generate the evaluation report of the patient; and providing said pulse oximetry data signals to computing circuitry that responds to the received pulse oximetry data signals by identifying a respiratory event of the patient, wherein the computing circuitry identifies said respiratory event in response to detecting pulse oximetry data signals that indicate a threshold level of oxyhemoglobin desaturation;

wherein the threshold level of oxyhemoglobin desaturation is variable, and the variable threshold level is based on at least one of the following criteria: peak oxyhemoglobin saturation, nadir, and peak oxyhemoglobin resaturation.

71. A physiological monitoring system comprising:

a pulse oximetry sensor and circuitry that detects oxyhemoglobin saturation and pulse rate of the patient and produces corresponding pulse oximetry data signals;

a patient head movement sensor that produces a head movement and position data signal that indicates position and movement of the patient's head;

a microphone that produces a sound data signal that indicates detected sounds produced by said patient;

power means for providing electrical energy to said pulse oximetry sensor, said head movement sensor, and said microphone for operation; and memory means for storing the data signals produced by said pulse oximetry sensor, said patient head movement sensor, and said microphone;

means for removably affixing said pulse oximetry sensor, said patient head movement sensor, said microphone, said power means and said memory means to the patient's forehead, wherein said sensors and power means detect the patient's oxyhemoglobin saturation, pulse rate, head movement and sounds, and produce the corresponding data signals, thereby monitoring said patient's condition, and whereby all lead wires between the patient and the memory means are eliminated; and computing circuitry that receives said pulse oximetry data signals and identifies a respiratory event of the patient, wherein the computing circuitry identifies said respiratory event in response to detecting pulse oximetry data signals that indicate a threshold level of oxyhemoglobin desaturation.

72. A system as defined in claim 71, wherein values of the pulse oximetry data signal that indicate a threshold level of oxyhemoglobin desaturation are variable.

73. A system as defined in claim 71, whereby the threshold level of oxyhemoglobin desaturation required to determine a respiratory event is variable.

74. A system as defined in claim 71, wherein the threshold level of oxyhemoglobin desaturation is variable, and wherein the variable threshold level is based on a known relationship between the partial pressure of oxygen and oxyhemoglobin saturation.

75. A system as defined in claim 71, wherein the threshold level of oxyhemoglobin desaturation is variable, and the variable threshold level is based on at least one of the following criteria: peak oxyhemoglobin saturation, or nadir, or peak oxyhemoglobin resaturation.

76. A system as defined in claim 71, wherein the pulse oximetry sensor comprises an active pulse oximetry sensor that applies positive pressure on the patient.

77. A system as defined in claim 71, wherein said means for affixing said pulse oximetry sensor, said patient head movement sensor, and said power means to the patient's forehead comprises an adjustable strap.

* * * * *

UNITED STATES PATENT AND TRADEMARK OFFICE
CERTIFICATE OF CORRECTION

PATENT NO. : 6,811,538 B2
DATED : November 2, 2004
INVENTOR(S) : Philip R. Westbrook et al.

It is certified that error appears in the above-identified patent and that said Letters Patent is hereby corrected as shown below:

Column 10,
Line 41, delete "ate" and insert -- rate --.

Column 17,
Line 4, after "($N_{max}$-$N_{min}$)/" insert -- ( --.

Column 18,
Line 48, delete "s".

Column 26,
Line 15, delete "reference" and insert -- referenced --.

Column 27,
Line 25, delete "of the patient".

Column 28,
Line 31, delete "oxyhemoalobin" and insert -- oxyhemoglobin --.
Line 63, delete "of the patient".

Column 30,
Line 7, delete "of the patient".

Signed and Sealed this

Twenty-sixth Day of April, 2005

JON W. DUDAS
*Director of the United States Patent and Trademark Office*

UNITED STATES PATENT AND TRADEMARK OFFICE
CERTIFICATE OF CORRECTION

PATENT NO.      : 6,811,538 B2                              Page 1 of 1
APPLICATION NO. : 10/040937
DATED           : November 2, 2004
INVENTOR(S)     : Philip R. Westbrook et al.

It is certified that error appears in the above-identified patent and that said Letters Patent is hereby corrected as shown below:

Column 1, lines 15-16, delete "The invention described herein was supported in part by NIH Grant HL66826-01" and insert instead
-- This invention was made with government support under NIH Grant HL66829-01 --

Signed and Sealed this

Eleventh Day of May, 2010

David J. Kappos
*Director of the United States Patent and Trademark Office*